US009387036B2

(12) United States Patent  (10) Patent No.: US 9,387,036 B2
Turner et al.  (45) Date of Patent: *Jul. 12, 2016

(54) APPARATUS AND METHOD FOR SELECTIVELY HEATING A DEPOSIT IN FATTY TISSUE IN A BODY

(75) Inventors: Paul F. Turner, Bountiful, UT (US); Mark Hagmann, Salt Lake City, UT (US)

(73) Assignee: Pyrexar Medical Inc., Salt Lake City, UT (US)

(*) Notice: Subject to any disclaimer, the term of this patent is extended or adjusted under 35 U.S.C. 154(b) by 1002 days.

This patent is subject to a terminal disclaimer.

(21) Appl. No.: 12/646,729

(22) Filed: Dec. 23, 2009

(65) Prior Publication Data

US 2010/0100092 A1  Apr. 22, 2010

Related U.S. Application Data

(63) Continuation-in-part of application No. 12/152,513, filed on May 14, 2008, now Pat. No. 8,423,152, which is a continuation-in-part of application No. 12/479,670, filed on Jun. 5, 2009, now abandoned.

(60) Provisional application No. 60/930,329, filed on May 14, 2007.

(51) Int. Cl.
*A61N 5/00* (2006.01)
*A61B 18/18* (2006.01)
(Continued)

(52) U.S. Cl.
CPC .............. *A61B 18/18* (2013.01); *A61B 18/1815* (2013.01); *A61N 5/025* (2013.01); *A61B 2018/00464* (2013.01)

(58) Field of Classification Search
CPC .......... A61N 5/02; A61N 5/025; A61N 5/045; A61N 1/40; A61N 1/44
USPC .......................................................... 607/101
See application file for complete search history.

(56) References Cited

U.S. PATENT DOCUMENTS 4,640,280 A * 2/1987 Sterzer ........................ 607/154
5,097,844 A * 3/1992 Turner ........................ 607/156
(Continued)

OTHER PUBLICATIONS

Denardo et al., "Thermal dosimetry predictive of efficacy of 111In-ChL6 nanoparticel AMF-induced thermoablative therapy for human breast cancer in mice" Journal of Nuclear Medicine, Mar. 2007, vol. 48, No. 3, pp. 437-444.

(Continued)

*Primary Examiner* — Ronald Hupczey, Jr.
(74) *Attorney, Agent, or Firm* — Thorpe North & Western, LLP

(57) ABSTRACT

Heat treatment is applied to tissue in need of such treatment which is surrounded by tissue not in need of such treatment, by positioning a deposit within the surrounding tissue adjacent the tissue in need of treatment. The dielectric constant and/or the conductivity of the deposit is greater than that of the surrounding tissue. A radio frequency antenna or antenna array directs a radio frequency signal at a selected frequency into the deposit. The deposit has a diameter within a range of about 0.5 times to about 0.16 times the wavelength of the radio frequency signal within the surrounding tissue. The deposit is heated, at least partially through resonant heating, to a temperature greater than the surrounding tissue to apply heat treatment to the tissue in need of treatment. The deposit may take the form of a balloon of a Mammosite® type device to provide hyperthermia treatment in conjunction with radiation treatment of a breast after a lumpectomy.

31 Claims, 8 Drawing Sheets

(51) Int. Cl.
*A61N 5/02* (2006.01)
*A61B 18/00* (2006.01)

(56) References Cited

U.S. PATENT DOCUMENTS

| | | | |
|---|---|---|---|
| 5,231,997 | A | 8/1993 | Kikuchi et al. |
| 5,540,737 | A | 7/1996 | Fenn |
| 5,690,109 | A * | 11/1997 | Govind et al. ............... 600/411 |
| 5,928,159 | A | 7/1999 | Eggers et al. |
| 6,131,577 | A | 10/2000 | Nicholson |
| 6,163,726 | A | 12/2000 | Wolf |
| 6,275,738 | B1 | 8/2001 | Kasevich et al. |
| 6,347,251 | B1 | 2/2002 | Deng |
| 6,358,246 | B1 | 3/2002 | Behl et al. |
| 6,391,026 | B1 | 5/2002 | Hung et al. |
| 6,413,204 | B1 | 7/2002 | Winkler et al. |
| 6,425,912 | B1 | 7/2002 | Knowlton |
| 6,468,273 | B1 | 10/2002 | Leveen et al. |
| 6,470,217 | B1 | 10/2002 | Fenn et al. |
| 6,494,844 | B1 | 12/2002 | VanBladel et al. |
| 6,500,174 | B1 * | 12/2002 | Maguire et al. ............... 606/41 |
| 6,690,976 | B2 * | 2/2004 | Fenn et al. .................... 607/101 |
| 6,712,816 | B2 | 3/2004 | Hung et al. |
| 6,725,095 | B2 | 4/2004 | Fenn et al. |
| 6,768,925 | B2 | 7/2004 | Fenn et al. |
| 6,904,323 | B2 | 6/2005 | Samulski |
| 6,923,754 | B2 * | 8/2005 | Lubock ............................. 600/3 |
| 6,945,942 | B2 | 9/2005 | Van Bladel et al. |
| 7,354,391 | B2 | 4/2008 | Stubbs |
| 7,510,555 | B2 | 3/2009 | Kanzius |
| 8,423,152 | B2 * | 4/2013 | Turner ................... A61B 18/18 607/101 |
| 2005/0251234 | A1 | 11/2005 | Kanzius et al. |
| 2006/0142749 | A1 * | 6/2006 | Ivkov .............................. 606/27 |
| 2006/0190063 | A1 * | 8/2006 | Kanzius ....................... 607/101 |
| 2006/0269612 | A1 | 11/2006 | Xiang et al. |
| 2007/0060990 | A1 * | 3/2007 | Satake .......................... 607/101 |
| 2007/0168001 | A1 | 7/2007 | Xiang et al. |
| 2008/0045865 | A1 | 2/2008 | Kislev |
| 2008/0319437 | A1 * | 12/2008 | Turner et al. .................... 606/33 |
| 2009/0062788 | A1 * | 3/2009 | Long et al. ....................... 606/41 |
| 2009/8030664 | | 12/2009 | Turner |

OTHER PUBLICATIONS

Dewhirst, "Hyperthermia and nanotechnology—a note from the editor-in-chief" Int. J. Hyperthermia, Sep. 2008, vol. 24 No. 6, pp. 449-450.

Gannon et al.; Carbon Nanotube-enhanced Thermal Destruction of Cancer Cells in a Noninvasive Radiofrequency field; Wiley InterScience (www.interscience.wiley.com) Oct. 24, 2007; pp. 2654-2665.

Gannon et al.; Intracellular Gold Nanoparticles Enhance Non-Invasive Radiofrequency Thermal Destruction of Human Gastrointestinal Cancer Cells; Journal of Nanobiotechnology 2008; 6:2; 9 pages.

Huang et al., "The influence of single-walled carbon nanotube structure on the electromagnetic interference shielding efficiency of its epoxy composites" 2007, 7 pages.

Ivkov et al., "Application of high amplitude alternating magnetic fields for heat induction of nanoparticles localized in cancer" Clin Cancer Res, 2005, pp. 7093-7103, vol. 11.

Klingeler et al., "Carbon nanotube based biomedical agents for heating, temperature sensing and drug delivery" Int. J. Hyperthermia, Sep. 2008, pp. 496-505, vol. 24, No. 6.

Laloup; http://www.wired .com/medtech/health/news/2008/04/kanzius_therapy; Apr. 13, 2008; 2 pages.

McLachlan et al., "The AC and DC conductivity of nanocomposites" Journal of Nanomaterials, 2007, vol. 2007, 9 pages.

Mdarhri et al., "Microwave properties of multiwall carbon nanotubes filled polymers" Journal of microwaves and optoelectronics, Jun. 2007, pp. 38-43, vol. 6, No. 1.

Moran et al.; Size Dependent Joule Heating of Gold Nanoparticles Using Capacitively Coupled Radiofrequency Fields; Nano Res; 2009; vol. 2 pp. 400-405.

Ott et al., "Radiochemotherapy for bladder cancer" Clinical Oncology, 2009, pp. 557-565, vol. 21.

Sundararman et al; The Modification of Specific Absorption Rates in Interstitial Microwave Hyperthermia via Tissue-Equivalent Material; Int J Radiat Oncol Biol Phys; Sep. 1990; vol. 3; pp. 677-685.

Thiesen et al., "Clinical applications of magnetic nanoparticles for hyperthermia" Int. J. Hyperthermia, Sep. 2008, vol. 24 No. 6 pp. 467-474.

USAF School of Aerospace Medicine; Radiofrequency Radiation Dosimetry Handbook; Report SAM-TR-76-35; Sep. 1976; 10 pages.

USAF School of Aerospace Medicine; Radiofrequency Radiation Dosimetry Handbook; Second Edition Report SAM-TR-78-22; May 1978; 9 pages.

Barry et al.; Challenges in the Development of Magnetic Particles for Therapeutic Applications; Int J. Hyperthermia; Sep. 2008; vol. 24, No. 6; pp. 451-466.

Sandler et al.; Ultra-Low Electrical Percolation Threshold in Carbon-Nanotube-Epoxy Composites; Polymer; 2003; vol. 44; pp. 5893-5899.

Von Maltzahn et al; Computationally Guided Photothermal Tumor Therapy Using Long-Circulating Gold Nanorod Antennas; Cancer Res; May 1, 2009; vol. 69, No. 9; 9 pages.

U.S. Appl. No. 12/479,670, filed Jun. 5, 2009; Paul F. Turner; office action issued Oct. 17, 2011.

U.S. Appl. No. 12/152,513, filed May 14, 2008; Paul F. Turner; office action issued Dec. 23, 2011.

U.S. Appl. No. 12/646,729, filed Dec. 23, 2009; Paul F. Turner; office action issued May 21, 2012.

U.S. Appl. No. 12/479,670, filed Jun. 5, 2009; Paul F. Turner; office action issued Mar. 29, 2012.

U.S. Appl. No. 12/479,670, filed Jun. 5, 2009; Paul F. Turner; office action dated Feb. 14, 2013.

U.S. Appl. No. 12/152,513, filed May 14, 2008; Paul F. Turner; notice of allowance dated Dec. 26, 2012.

* cited by examiner

APPARATUS AND METHOD FOR SELECTIVELY HEATING A DEPOSIT IN FATTY TISSUE IN A BODY

CROSS-REFERENCE TO RELATED APPLICATIONS AND CLAIM OF PRIORITY

This is a continuation-in-part of U.S. patent application Ser. No. 12/152,513, filed on May 14, 2008, now U.S. Pat. No. 8,423,152, issued Apr. 16, 2013, which claims priority to U.S. Provisional Patent Application Ser. No. 60/930,329 filed on May 14, 2007. This is also a continuation-in-part of U.S. patent application Ser. No. 12/479,670, filed on Jun. 5, 2009, now abandoned. All of the above are herein incorporated by reference in their entirety.

TECHNICAL FIELD

The present invention generally relates to inducing hyperthermia or other heating in a desired target in a living body, such as in cancerous tumor tissue or other diseased tissue in the living body.

BACKGROUND

Certain types of cancerous tumors, such as breast cancer tumors, particularly inflammatory and locally advanced tumors, often resist traditional treatments. It has been statistically shown that sixty to seventy percent of victims of such breast tumors do not survive past five years. The efficacy of conventional methods of treating cancer, such as radiotherapy and chemotherapy, is limited due to necessary constraints on dosage amounts for safety.

For example, it is known that chemotherapy can be applied in sufficient amounts to kill virtually all cancer cells of a tumor. However, the amounts of chemotherapy needed to achieve this can be high enough to cause poisoning of the patient and/or undue side effects. As another example, the intensity of an x-ray beam applied in accordance with radiotherapy cannot be set at an intensity that will damage nearby critical organs and surrounding healthy tissues. Accordingly, there is an ongoing need to develop techniques that enhance existing cancer-related therapeutic procedures so as to increase their effectiveness without increasing the risk of damage to healthy tissue and causing additional discomfort for cancer patients, and also for developing new methods of cancer treatments.

It has been found that the effectiveness of radiation therapy and chemotherapy can be increased by heating a tumor or other cancer tissue immediately before, during, or immediately after the application of radiation in radiation therapy or the application of cancer treating chemicals in chemotherapy. This increased effectiveness can reduce the amount of radiation or chemicals needed for successful radiation therapy or chemotherapy thereby making radiation therapy or chemotherapy available to patients who might not be able to tolerate such treatment otherwise. When heating is combined with radiation therapy or chemotherapy, it is desirable to maintain the temperature of the treated diseased tissue within the range of about 42 to 45 degrees C. Treatment within this controlled temperature range is usually referred to as hyperthermia.

Forms of thermal therapy that kill diseased tissue with heating alone are generally referred to as coagulation or ablation. To adequately eradicate a cancerous tumor with only the application of heat, it is generally necessary to heat the diseased tissue to at least about 55 degrees C., and typically above about 60 degrees C., for exposure times sufficient to kill the cells, typically for greater than about one minute. With such coagulation or ablation treatments, it is important to sufficiently heat the diseased tissue to be treated but to limit heating of the normal tissue surrounding the diseased tissue.

Breast tumors that have grown to a size of about 3 cm to about 5 cm are particularly hard to treat and are hard to remove surgically, generally requiring removal of the breast to remove the tumor. Alternative treatments for such tumors are needed.

One recent approach toward improving cancer therapy is to subject a tumor to a hyperthermia treatment, i.e., heating of the tumor. As indicated, the application of heat to cancer cells has been found to increase the efficacy of certain types of therapies for various proposed reasons. Microwave and radio frequency (RF) energy sources have been employed to conduct hyperthermia treatment. Microwave energy has been applied to tumors using waveguides. However, the relatively high frequencies at which microwaves propagate are generally not suitable for deep penetration into tissue.

RF energy at a lower frequency has also been utilized in some instances, and has the potential to achieve greater penetration due to its relatively lower frequencies. However, both microwave and RF techniques have typically used invasive elements, such as wires, catheters, lumens, probes, receivers, and the like. These invasive elements are usually inserted or embedded in the tumor to be treated to ensure proper coupling and focusing of the electromagnetic energy at the tumor site. The use of invasive elements adds complexity to the procedure and is a source of discomfort for patients. Examples of invasive heating techniques using microwave and RF energy are disclosed in U.S. Pat. Nos. 5,928,159; 6,275,738; 6,358,246; 6,391,026; 5,540,737, and 6,468,273.

One prior method for hyperthermia treatment involves the use of phased arrays of dipoles surrounding portions of a body in which a selected portion, such as a tumor, is desired to be heated. The dipoles are operated in a coherent phase or at least a synchronous phase relationship to enable selective targeting of deep tissue tumor masses by controlling the power and relative phase applied to the array of dipoles. These dipoles couple their RF or microwave energy to the body through typically deionized water media as it is high in dielectric constant similar to most of the body tissues but is lower in electrical conductivity so it provides small wavelengths but low power absorption. The antenna arrays surrounding such tissue structures have generally been in concentric arrays using lower frequencies with long wavelengths or have been at high frequencies, at or near microwave frequencies, but not in arrangements that would produce selective resonant behavior in tumors of the breast nor create circular polarization that would improve uniformity of such tissue target heating.

Samulski, in U.S. Pat. No. 6,904,323, described the use of phased array dipoles that are placed around a cavity containing fluid such as water and where a human breast containing a cancerous tumor can be submerged and heated by the surrounding dipole antennas. This method uses rather low frequencies that produce a very large wavelength in both high water tissues of the body and in low water content tissues such as mammary fat. The operation, typically at a frequency of about 140 MHz, results in a wavelength in fatty tissue of about 86 cm and in muscle tissues of about 22.9 cm.

There remains a need for an improved method and apparatus for more selectively inducing hyperthermia in tumors and malignant tissue or for otherwise providing selective heating of tissue in need of hyperthermia or other heat treatment, particularly for such tissue that reside within a breast or other portion of a body where such tumor is surrounded by fatty low water tissue, while avoiding or at least decreasing the potential of excessively heating the surrounding tissue.

SUMMARY

An apparatus and method for providing hyperthermia treatments to a body portion having fatty tissue surrounding a deposit such as a tumor, cyst, or high conductivity implant in the body portion is disclosed. In one embodiment, the apparatus includes a cavity for receiving a protruding body portion, such as a breast, having the deposit to be heated therein. A radio frequency signal generator operable to generate a radio frequency signal is used. The signal generator can output a radio frequency signal that will have a selected wavelength within the fatty tissue. The wavelength in the fatty tissue is in a range of about 3.75 to 2.25 times a diameter of the deposit to be heated. In one embodiment, a radio frequency antenna array is used to direct the radio frequency signal into the protruding body portion, such as the breast, to create a circularly polarized radio frequency electromagnetic field to selectively heat the deposit to a temperature greater than the surrounding fatty tissue through resonant heating within the deposit from the radio frequency signal having the selected wavelength. A linearly polarized electromagnetic field can also be used.

The deposit can be an area of diseased tissue in the fatty tissue, such as a tumor in a breast, which is to be heated for treatment, or the deposit can be an implant of material into the fatty tissue. In either case, the deposit is selectively heated to a temperature greater than the surrounding fatty tissue, at least in part, through resonant heating. One embodiment of the invention uses a fluid filled balloon in a breast, such as provided by a Mammosite® type device after a lumpectomy, as the deposit to be heated, with the heated deposit heating and providing heat treatment to tissue surrounding the deposit. An injectable medium operable to be injected into the deposit can be used to increase at least one of a dielectric value and a conductivity value of the deposit. The injectable medium is selected to increase a specific absorption rate of the radio frequency signal within the deposit relative to the surrounding tissue.

In a second embodiment, a radio frequency antenna can be positioned in the deposit to again selectively heat the deposit to a temperature greater than the surrounding tissue. Again, the radio frequency signal will have a selected wavelength within the fatty tissue that is in a range of about 3.75 to 2.25 times a diameter of the deposit to selectively heat the deposit at least partially by resonant heating.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
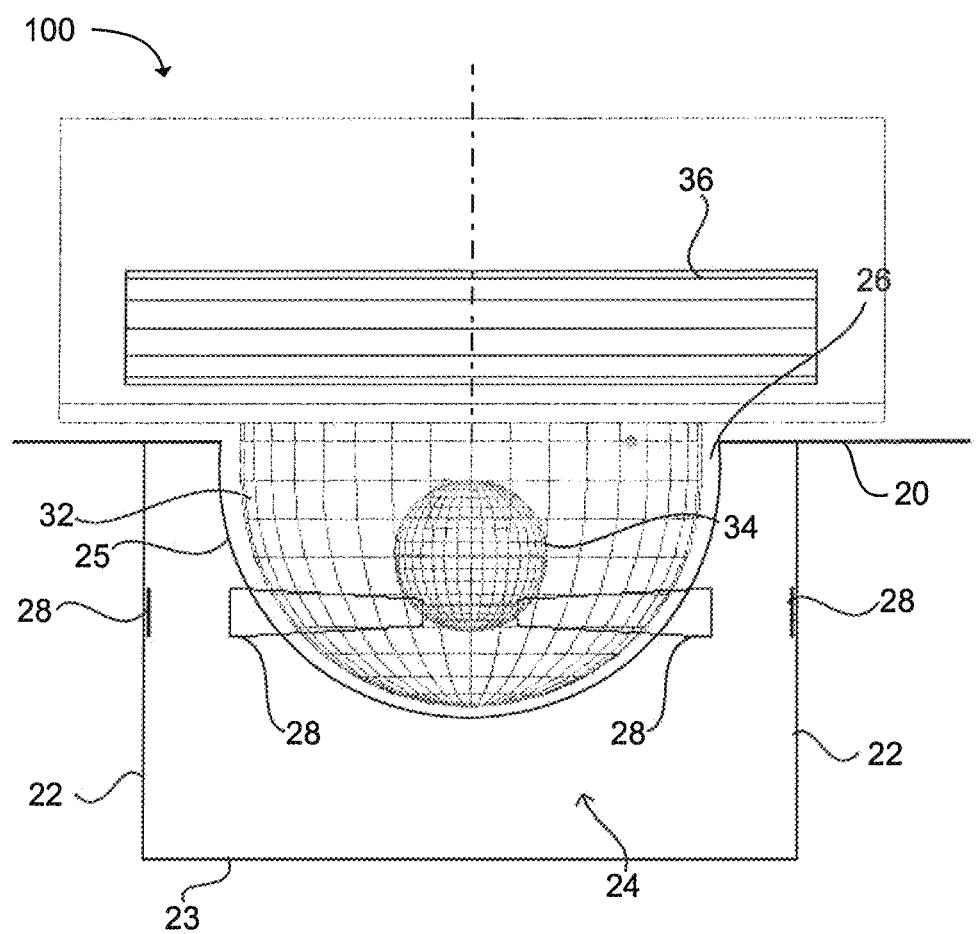
FIG. 1 is a side schematic illustration of an apparatus in accordance with an embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENTS

It has been found that a deposit such as a tumor, cyst, or high conductivity implant in a body portion having fatty tissue surrounding the deposit, can be selectively heated by directing RF or microwave energy to the body part with a frequency high enough to promote resonant energy absorption in the deposit, such as tumor tissue, as compared to the surrounding tissue. Such selective heating is particularly successful where the deposit, such as tumor tissue, to be heated has relatively high water content compared to the surrounding non-tumor tissue. This enhanced energy absorption relates to a sub-resonant condition behavior of the relatively high water content tissue due to the fact that low water content tissues of the body has rather low electrical conductivity, dielectric constant, and energy absorption with depth as compared to higher water content tissue such as muscle and tumor tissues. The lower dielectric constant results in a longer wavelength in such tissues for all frequencies in the RF and microwave frequency range, with a shorter wavelength in the higher dielectric constant tumor tissue. The higher conductivity tissue can resonate in a relatively small cavity, such as a tumor. The conditions for resonance are generally present in deposits, such as tumors, in a human breast, where the high water content deposit is surrounded by fatty mammary tissue generally of low water content.

Resonance is a phenomenon that is used to receive and amplify electromagnetic field waves in standard RF and microwave antennas. The antennas are electrical conductors used to enhance electrical currents induced when exposed to electromagnetic fields that have a wavelength that is n times a ½ ratio of the size of the antenna, where n is a positive integer. The strongest whole object resonance can occur when the wavelength is two times the antenna length for a wire antenna (n=1). The use of resonance to amplify an electromagnetic field has not been reported or studied for tissue structures submerged in the human body. The inventors have discovered that such relationships do occur and can be utilized to provide enhanced and even selective heating of more conductive and higher dielectric constant tissue masses that are surrounded by tissue having less electrical conductive and lower dielectric constant.

Theoretically, the resonance phenomenon can be applied to selectively heat various targets or deposits in a human body where the deposit to be selectively heated is surrounded by tissue having different dielectric constants and conductivity properties. However, for such resonant heating to occur, the deposit to be heated should have a size, such as having a diameter, that is about one third the wavelength of the radio frequency radiation wavelength in the tissue surrounding the deposit to be heated. Thus, the deposits that can be heated selectively through resonant heating vary with the size of the deposit, the difference in the dielectric constant and/or the conductivity between the deposit and the surrounding tissue, and the frequency of the radiation being used. Thus, the size of the deposit to be treated will in most cases determine the frequency needed to create resonant heating in the deposit.

The term radio frequency (RF) generically means electromagnetic radiation with an alternating electric current. It has been common in recent years to define RF extending from frequencies as low as 3 Hz to 300 GHz. The microwave frequency range has been defined to start at various lower frequencies from as low as 300 MHz for some sources and starting at 1000 MHz for others. Therefore, the terms are not very specific to use. Use of a specific frequency range becomes important when referring to a resonant type of phenomena that leads to selective energy absorption. The term radio frequency or RF will generally be used in this specification, with specific frequencies or frequency ranges of the alternating electric current in the electromagnetic energy disclosed.

One aspect of the present invention is the use of this special resonance phenomena to provide selective heating of a high water content tumor mass that is surrounded by larger, drier tissue, such as fat tissues. An advantageous application of the present invention is the enhanced level of RF or microwave energy absorption within a tumor of a size between about 3 cm and about 6 cm of high water content tissue as compared to the surrounding fatty tissues when using microwave radiation at a frequency of about 915 MHz. The inventors have found this selective resonant heating is particularly applicable to the treatment of larger cancerous tumors or other deposits in the human breast. Tumors or other deposits in the human breast are considered as larger when having at least one diameter of about 3 cm or more. These larger breast tumors of between about 3 cm and about 5 cm are common and are difficult to treat. The present invention provides selective heating of a 3 to 5 cm or larger high water content tumor mass that is surrounded by drier tissue such as fatty mammary tissue, at a frequency of 915 MHz.

One embodiment of an apparatus 100 for providing hyperthermia treatment for selectively heating tumors located in a human female breast is illustrated in FIG. 1. The apparatus comprises an applicator body 25 and a plurality of antennas 28. The applicator body has a concave profile extending from an aperture 26, and defines an open cavity 24 for receiving RF or microwave circularly or elliptically polarized waves. The antennas are operatively associated with the applicator body and are arrayed for transmitting RF or microwave waves at respective selected amplitudes and relative phases into the cavity. The cavity is typically a fluid filled cavity. The electromagnetic energy from the arrayed antennas is generally directed toward tumor-containing tissue to produce a circularly or elliptically polarized field that will be selectively absorbed by the high water content tissues of a tumor of a size that is partially resonant with the applied fields and their wavelength in the surrounding low water content fatty tissue.

Without any additional enhancements of the deposit, the amount of resonant energy that is absorbed in a deposit such as a cancerous mass can be optimized by selecting a specific wavelength of electromagnetic radiation in the low water content media that is approximately 3 times greater than a diameter of the high water deposit to be heated. However, in most countries, the use of the electromagnetic spectrum is heavily regulated. The radio frequency spectrum has been divided into bands, with each band or frequency typically allowed to be used only for a specific application. The frequency of 915 MHz is an approved frequency for use in hyperthermia treatments in the United States and many other countries.

The wavelength of RF radiation at a frequency of 915 MHz is approximately 14 cm in the fatty tissues of the female breast. This mammary fatty tissue is the dominant tissue of the breast. The wavelength in high water tissues such as muscle tissue or tumor tissue at 915 MHz is approximately 4.36 cm. The table below shows typical values for the RF frequency of 915 MHz for wavelength, penetration, and conductivity in different types of tissue, as published by various sources.

| Source | Tissue | Freq (MHz) | Diel. | Cond. S/m | Wave length (cm) | Penetration (cm) |
|---|---|---|---|---|---|---|
| Guy | Breast/Fat | 915 | 5.6 | .056-.15 | 13.7 | 17.7 |
| Guy | Muscle | 915 | 51 | 1.60 | 4.46 | 3.04 |
| IFAC | Breast/Fat | 915 | 5.42 | 0.050 | 14 | 25 |
| IFAC | Muscle | 915 | 55 | .948 | 4.35 | 4.2 |
| Gabriel | Breast/Fat | 915 | 5.42 | .050 | 14 | 25 |
| Gabriel | Muscle | 915 | 55 | .948 | 4.35 | 4.2 |

Tissue Value Comparisons of Dielectric Constant

| Tissue | Freq (MHz) | Guy | IFAC | Gabriel | Joines | Pethig |
|---|---|---|---|---|---|---|
| Breast/Fat | 915 | 5.6 | 5.42 | 5.42 | 15 | 5.6 |
| Muscle | 915 | 51 | 55 | 55 | 57.1 | 46 |

Tissue Value Comparisons of Conductivity (S/m)

| Tissue | Freq (MHz) | Guy | IFAC | Gabriel | Joines | Pethig |
|---|---|---|---|---|---|---|
| Breast/Fat | 915 | .056-.15 | .050 | .050 | .18 | .083 |
| Muscle | 915 | 1.60 | .948 | .948 | 1.16 | 1.28 |

The wavelength of RF radiation at a frequency of 120 MHz, another frequency that is sometimes available for hyperthermia treatment use, is between approximately 70 to 80 cm in low water fatty tissue and between approximately 22 to 27 cm in the typical high water content tissues of the human body. Therefore, to provide any resonant heating of a tumor or other deposit surrounded by fatty tissue such as the fatty mammary tissue of the breast, the tumor would have to have a size of between approximately 22 to 27 cm. Therefore, the frequency of 120 MHz can not be used to provide resonant heating of a tumor in the fatty tissue of the breast. However, when a tumor or other deposit is located in higher water content tissue as compared to fatty tissue, the wavelength of the 120 MHz signal in such other higher water content tissue, such as muscle tissue, is much shorter than in the low water mammary fatty breast tissue. Therefore, if a tumor or other deposit is located in higher water tissue rather than fatty tissue, the wavelength in the high water tissue, such as muscle tissue where the 120 MHz signal has a wavelength of approximately 22 to 27 cm, could selectively heat a tumor surrounded by that higher water tissue as long as the dielectric constant and/or conductivity of the tumor tissue is different than the muscle tissue in which it is located. The 120 MHz wavelength, radio frequency energy can be directed deep into the body, including the body center, using phased array antennas. For example, a phased array hyperthermia treatment system such as the BSD-2000 available from BSD Medical Corporation may be used to direct RF radiation to a deposit within the body to selectively heat a deposit. As used herein, a deposit is intended to include a tumor, a cyst, or other type of growth, or an implant, that is surrounded by relatively healthy tissue. Thus, the selective heating of a deeper deposit can also be enhanced through the use of resonant heating.

As previously discussed, electromagnetic frequencies having a selected wavelength can resonate within an object of a selected size. When the object is an inner object having a higher conductivity and/or a higher relative dielectric constant that is contained within a larger object having a lower relative conductivity and/or a lower relative dielectric constant, the smaller inner object may receive substantially more power from an electromagnetic field due to its size and conductivity.

For example, in a tumor contained within a female breast, the tumor can have a diameter approaching 4.5 cm. This tumor, which has a higher water content than the surrounding fatty breast tissue, may therefore experience a self resonant condition leading to increased tumor heating relative to the fatty breast tissue due to the increased resonant currents at a frequency of 915 MHz. With no additional changes made to a tumor, this resonant behavior may also be expected to occur at diameters larger than this but with less intensity. So it is reasonable to consider that tumors near this resonant size condition of approximately between about 3 cm to about 6 cm in diameter may experience some selective heating due to the resonance of the tumor mass that is surrounded by fatty mammary tissue.

In an example of a tumor surrounded by high water content tissue, wherein the tumor has even higher water content or otherwise has a higher conductivity or higher relative dielectric constant, the optimal resonant tumor diameter can have a diameter approaching 7 to 8.6 cm when a 120 MHz radio frequency signal is used. Such a tumor may therefore experience a self resonant condition leading to increased tumor heating relative to the surrounding body tissue due to the increased resonant currents at a frequency of 120 MHz. Without additional enhancements to the tumor, this resonant behavior may also be expected to occur at diameters less than or larger than this diameter range, but with a decreased amount of resonance resulting in a decrease in the selective heating due to resonance. Therefore, it is reasonable to consider that tumors near this resonant size condition of approximately between 5 to 11 cm in diameter, and located in high water surrounding tissue may experience some selective heating at a deeper penetrating frequency of 120 MHz due to the resonance of the conductivity enhanced deposit typical of a tumor mass that contain a relatively high amount of water that is surrounded by normal body tissues that contain a relatively lower amount of water. In some cases it is possible to inject material into the tumor or other deposit to increase its conductivity or dielectric constant to enable the increased resonate heating of the tumor or other deposit. If the deposit is implanted into the surrounding tissue, it is possible to select a material for the transplanted deposit that has the required higher conductivity and/or dielectric constant.

This resonate heating behavior is similar to a resonant antenna in free space. The phenomena of body resonance for a human body was observed and reported in a U.S. Air Force commissioned study at the University of Utah in 1976, as reported in SAM-TR-76-35 and SAM-TR-78-22 (1978) page 101, which is herein incorporated by reference. In this report, it is shown that a prolate spheroidal model of a chicken egg would be of major axis size 5.8 cm and minor size diameter of 4.4 cm. When the chicken egg is located in an air medium and exposed to a 2 GHz field it becomes resonant with the field. On resonance in an electromagnetic field having an intensity of 1 milliwatt per centimeter squared ($mW/cm^2$), the specific absorption rate (SAR) of the egg is between 0.35 to 0.46 Watts/kg. At higher frequencies, where the egg diameter is no longer resonant due to the shorter wavelength of the RF signal, the absorption drops to about 0.11 W/kg.

The free space wavelength of an RF signal at a frequency of 2 GHz is 15 cm. The resonant diameter size of the spheroid object is between 0.293 to 0.386 times the wavelength, or in other words, approximately one fourth to one third of the wavelength. The free space wavelength of an RF signal at a frequency of 915 MHz is approximately 32.8 cm. The spherical resonance size for 915 MHz when surrounded by free space would be expected to be between 9.6 to 13.0 cm. This is calculated based on simple frequency scaling. The spherical resonance size for 120 MHz when surrounded by free space is between 73.0 cm to 99.0 cm.

For the condition that a spheroid, such as a cancerous tumor having a higher conductivity and dielectric value than the surrounding tissue, is contained within a uniform media such as fatty breast tissue that has a dielectric constant greater than free space, the resonant conditions can occur for a smaller spheroid that is scaled by the ratio of the wavelength differences. For example, the wavelength of the fatty breast tissue for a 915 MHz signal is approximately 14 cm. The same RF signal in free space is approximately 32.8 cm. Thus, the ratio of the wavelength of the signal in the breast tissue relative to the signal in free space is approximately 0.427.

Based on this ratio, the size of such an unaltered spheroid tumor in a fatty mammary tissue region would be between 4.1 cm to 5.5 cm to enable resonance to occur for an electromagnetic signal having a frequency of 915 MHz. The resonance behavior was shown in the Air Force reports to be rather broad. An increased specific absorption rate of approximately four times can occur in a resonant body based on the increase in absorption of the electromagnetic field due to the resonant dimensions of the body relative to the wavelength of the signal in the body. The frequency bandwidth to half the peak value of the resonant phenomena was shown to be about two times the resonant frequency. Therefore, it would be expected for an RF signal at a frequency of 915 MHz that the size range of a resonant body, having an unaltered conductivity or dielectric value, which would at least double the SAR relative to an outer body, could range from a size of 2.7 to 11 cm. This would cover the range of most primary advanced breast cancerous tumors.

Further scaling of the curve disclosed on page 101 of the SAM report shows that when an object is much smaller than the resonant size the SAR in the smaller body drops off very rapidly with frequency. For example, a spheroid diameter that is 1/5.5 in size relative to the optimum resonant diameter has a SAR that is approximately one fifth the absorption value of the body and only 5% of the SAR at resonance. So a tumor at 5.5 cm in size on resonance at 915 MHz that had a 4 to 5 times increase in SAR due to resonance would have a SAR 20 times greater than that of a 1 cm diameter tumor. Therefore, this unique resonant condition would not favor small tumor heating in the breast at 915 MHz under these modeled conditions.

Although the breast is internally dominated by mammary fatty tissues, there are glandular, ductal and lobular networks that may provide very small but higher conductivity and dielectric pathways for these microwave currents to flow and concentrate. However, these networks do not dominate the tissue construction in the breast and therefore do not significantly alter the resonant behavior and conditions. Tissue structures such as ductal and lobular networks however may themselves have selective increased SAR due to their higher conductivity, thereby causing selective pathways for the microwave currents within the breast. Also, since the breast mammary tissues themselves are more conductive than free space, it should be expected that the resonant enhancement of the specific absorption rate in a tumor relative to the absorption rate of the surrounding breast material may not be as great as shown in the SAM report of the egg relative to air. The surrounding mammary tissue may lower the resonant behavior similar to resistive loading of a resonant electrical circuit.

The specific use of the 915 MHz frequency band that has a wavelength in mammary tissue of about 14 cm then can have the capability to excite a resonance in a higher water content tissue such as a malignant tumor that has a diameter of approximately 4.5 cm. Note that even though a 3.5 cm diameter tumor does not exactly meet this criteria for the most selective tumor absorption, such a diameter at those conditions is in a state to have some resonance enhancement, but the greatest enhancement would be in a tumor with a diameter that is about $\frac{1}{3}^{rd}$ of the wavelength in the mammary tissue. Fortunately, most advanced tumors of the breast that become difficult for successful surgical removal are those that exceed about 3 cm in diameter. Thus, this resonant phenomena, when properly created in these larger tumors, may provide a desirable option in treating such cancerous tumors of the breast. Additional enhancements to the phenomena can be achieved by selectively increasing tumor conductivity and dielectric values through injection of conductivity and dielectric enhancing media such as saline solution and nanoparticles. Nanoparticles capable of being injected into a tumor and distributed through tumor cells are currently being developed for sale in the marketplace.

A linearly polarized electromagnetic signal can be used to induce a resonant behavior in a tumor. Such is generally the optimal approach for devices such as the BSD-2000 system that uses deep phased array of dipoles surrounding the body. For deep body target deposits, a linearly polarized antenna array may be preferred to selectively heat a conductivity enhanced deposit target such as a cancerous tumor.

However, the use of linear polarization will tend to have a less uniform distribution of power within the tumor and even the mammary tissue and may result in undesirable hot spots in normal mammary tissue or cooler zones in the tumor. The use of elliptically or circularly polarized electromagnetic radiation to induce resonant heating in a tumor can usually provide more even heating in most situations.

Figure 2:
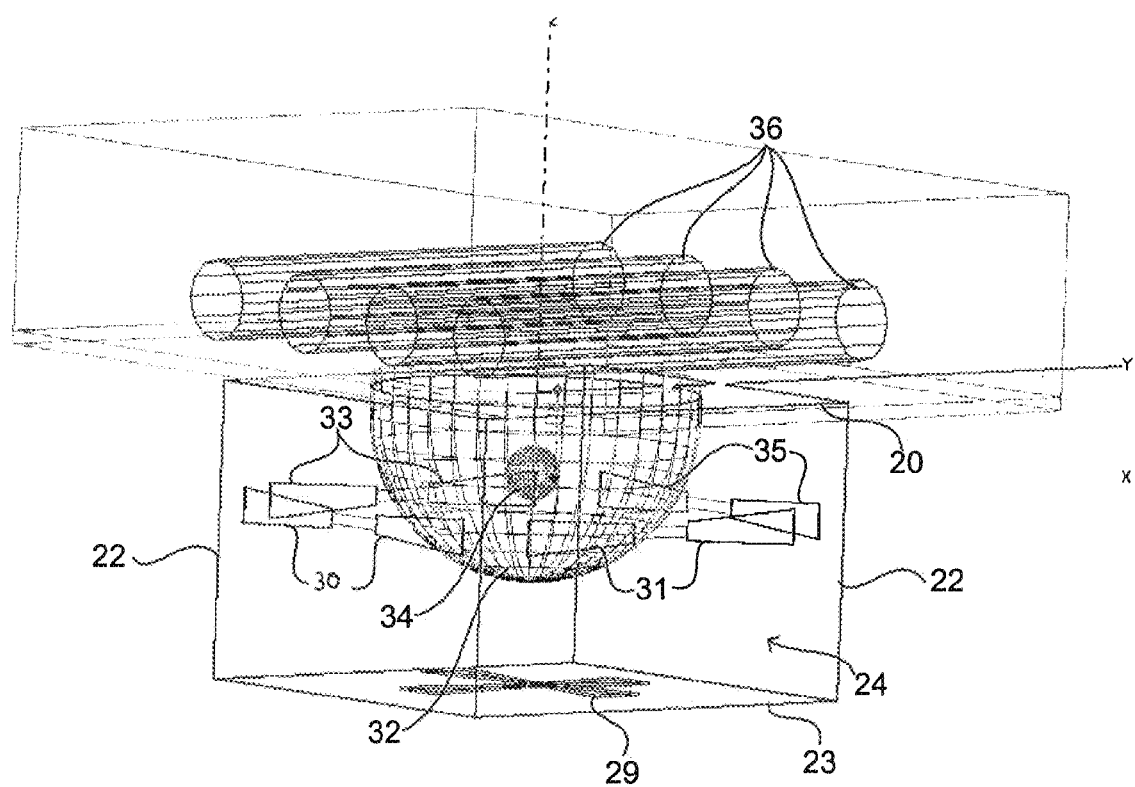
FIG. 2 is a perspective schematic illustration of an apparatus in accordance with an embodiment of the present invention.

Referring to FIGS. 1 and 2, an apparatus in one embodiment of the present invention includes an applicator body with a top peripheral surface 20, and side walls 22 with bottom wall 23 forming a cavity 24 which depends from an opening 26 in surface 20. An RF or microwave dipole antenna 28, shown as a bow tie dipole antenna, is positioned on each of the cavity walls 22 to form an antenna array surrounding the cavity 24. Additional dipole antennas 29, FIG. 2, may be provided on bottom wall 23 as part of the antenna array. In one embodiment, the applicator can be a portable unit with the peripheral surface 20 merely forming a top surface for the applicator.

In another embodiment, the applicator can be built into a larger unit with a patient support surface 20 being a relatively comfortable supporting surface. The patient can lie on the support surface in a position so that the protruding body part of the patient can be extended into and be received in cavity 24.

In the embodiment illustrated, a female patient having breast cancer with a breast tumor is positioned with the breast 32 to be treated extending into cavity 24. The breast tumor 34 is illustrated as substantially centered in the breast 32. Patient ribs are schematically represented as 36. Cavity 24 may be filled with a dielectric fluid to improve transmission of the RF or microwave energy to the breast. While the dielectric constant of the fluid is not critical, it has been found that fluids with a dielectric constant between about two and about eighty-one may be used satisfactorily. Water, with a dielectric constant of about seventy-eight, can be used. Oils, such as mineral oil or other oils with dielectric constants of about two to about four, vegetable oils, liquid silicones, or other fluids, such as for example propylene glycol or ethylene glycol, with dielectric constants between that of oils and water can also be used. A dielectric fluid that is substantially non-ionic and has a relatively low dielectric constant can minimize heating within the fluid, thereby allowing for greater cooling at a surface of the breast 32.

While the dielectric fluid(s) can be placed in the cavity 24 and come in direct contact with a breast or other body part placed in the cavity, it is usually preferred to provide a thin plastic or rubber membrane 25 in cavity 24 that separates the breast from the dielectric fluid and forms a bolus around the breast. The bolus membrane 25 can be formed by, for example, a silicone, urethane, or similar flexible membrane or film to prevent direct contact between the dielectric fluid and the body part. This protects the patient from contact with the fluid.

The dielectric fluid can also be used to control heating of the surface of the breast. The dielectric fluid may be at a lower relative temperature. Contact between the breast 32 and the bolus membrane 25 can be used to transfer excess heat from the outer breast tissue to the dielectric fluid. In one embodiment, the dielectric fluid in the cavity 24 may be circulated and cooled to provide surface cooling for the breast or other body part received in the cavity.

The size of the cavity 24 can vary. The cavity will typically be kept relatively close to the size of the body part to be received. Where a breast is to be treated, the perimeter of the cavity 24 to receive the breast works well when no more than about one and one half times the size of the base of the breast. A cavity with fifteen centimeter side walls has been found generally satisfactory for use with most breasts.

The applicator antennas 28 are connected in typical manner to a radio frequency signal source. The applicator antennas used can be of various types such as spiral antennas, waveguides, helical antennas, Tee Dipoles, and other common applicators used to radiate radio frequency radiation to heat tissue. The frequency and power output from the signal source can be controlled to provide a wavelength within the fatty mammary tissue where the diameter of the tumor is approximately $\frac{1}{3}^{rd}$ of the wavelength in the fatty tissue. For example, if the frequency of the RF signal supplied to the antennas is 915 MHz, that frequency will produce a wavelength in the normal fatty mammary breast tissue of about 14 cm. This wavelength in the fatty mammary breast tissue will then have the capability to excite a resonance in higher water tissue, such as in malignant tumor tissue, when the diameter of the malignant tumor tissue is approximately 4.5 cm. If the tumor to be treated has a diameter of about 4.5 cm, the tumor may exhibit full resonance excitement behavior and be selectively heated by the applied electromagnetic signal relative to the fatty breast tissue.

While it has been found that full resonance behavior occurs when the tumor diameter is approximately $\frac{1}{3}^{rd}$ of the wavelength in the fatty tissue, it has also been found that significant resonant behavior is exhibited within about plus or minus twenty-five percent of the one-third dimension. Thus, although a 3.5 cm diameter tumor does not exactly meet the one-third diameter criteria for the most selective tumor absorption, such a diameter still is in a state to have some resonance enhancement, and show significant selective heating over the fatty normal breast tissue.

Since, as indicated, most advanced tumors of the breast that become difficult for successful surgical removal are those that exceed about 3 cm diameter size, a microwave frequency of 915 MHz will produce significant selective heating of such tumors in a breast. This resonant phenomena, when properly created in these relatively larger tumors, can provide a desirable option in treating such cancerous tumors of the breast. Where allowed, the frequency of the applied microwave energy can be adjusted to provide substantially an exact one-third ratio between the tumor diameter and the wavelength in the normal fatty breast tissue. The desired wavelength to be produced in the surrounding tissue to provide substantially maximum resonant phenomena in the tumor is determined by multiplying the diameter of the tumor by $\pi$ (3.14).

In one embodiment, a single antenna, such as one of the antennas 28 shown in FIG. 1, or a single antenna such as the single antenna indicated as 30 in FIG. 2, can be used to direct radio frequency waves at a selected frequency into the breast 32 and tumor 34. However, emitting the radio frequency waves from a single antenna will provide more heat at a side of the breast toward the location of the antenna. To provide more even heat, a second antenna, such as antenna 35, FIG. 2, located opposite the first antenna 30 can be used. The radio frequency waves from the two antennas can be emitted in phase, thereby allowing the radio frequency waves to interfere within the cavity area 24. The two oppositely located antennas can provide heating to both sides of the tumor. Additionally, an interference pattern may form, resulting in relatively hot and cold areas across the breast and tumor. However, uneven absorption and reflection of the waves can still result in uneven heating of the tumor.

Alternately, to reduce uneven heating within the cavity 24 when only a first antenna 30, FIG. 2, is used, a second antenna 31 can be located with an emitting axis that is orthogonal to the emitting axis of antenna 30. The orthogonal antennas can be tuned to emit microwave radiation approximately ninety degrees out of phase relative to one other. The resulting output from the two antennas is a substantially circularly polarized electromagnetic field within the cavity area. However, again with this arrangement of two antennas, uneven absorption and reflection of the waves can still result in uneven heating of the tumor. To reduce uneven heating even further, a total of four antennas 30, 31, 33 and 35, i.e., orthogonal pairs of oppositely positioned antennas 30, 35 and 31, 33, FIG. 2, can be used to produce circularly polarized electromagnetic fields that substantially surround the breast to provide more even heating. The circular polarization produced can effectively stir the electromagnetic fields within the chamber, thereby reducing and eliminating hot spots that can develop and occur within the heating process. If the orthogonal pairs of antennas produce microwave radiation that is less than or greater than ninety degrees out of phase, the result will be elliptically polarized electromagnetic fields that can also be used to reduce and eliminate hot spots and cool spots to provide more even heat distribution within the breast 32 and tumor 34. A further antenna or antennas, shown as 29 in FIG. 2, can be located orthogonally to the antenna pairs 30, 35 and 31, 33 below the breast 32 in cavity area 24.

Figure 3A:
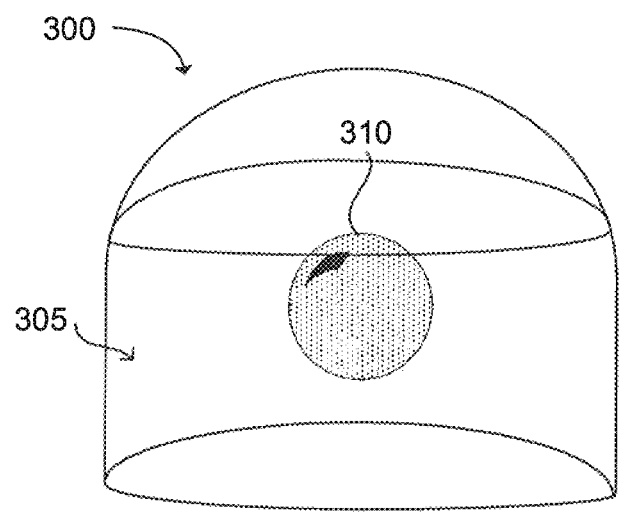
FIG. 3a is a perspective schematic illustration of a test phantom material configured to simulate a breast having a tumor in accordance with an embodiment of the present invention.

FIG. 3a shows a test phantom material 300 that was configured to simulate a breast formed substantially of fatty breast tissue 305 with a tumor 310 substantially centered therein. A phantom breast can be formed from a variety of different materials that are used to simulate the properties of the fatty breast tissue and a tumor having a higher water content. Materials are selected based on their similar properties to breast tissue in the absorption and reflection of radio frequency waves at a selected frequency, such as 915 MHz.

A plurality of different phantom breasts made of various substances were formed and tested using a test device that was configured substantially as illustrated in FIG. 2. One test phantom 300 was formed having an outer area 305 formed of paraffin wax mixed with 0.04% carbon by weight for a dielectric of 8.5 and a conductivity of 0.097 S/m. The wavelength of radio frequency waves at a frequency of 915 MHz in the outer paraffin area is about 11 cm. This wavelength divided by $\pi$ is about 3.6 cm. The inner area 310 was formed of a saline water based TX-150 gel material to simulate the makeup, electrical, and physical properties of a tumor.

Another test phantom 300 was formed using 1032 grams of wheat flour (64.5%), 464 grams of corn oil (29.9%), 4.1 grams of sodium chloride (0.256%), and 99 grams of water (6.2%) to form the outer area 305. The tumor phantom model 310 was comprised of 89.97% water, 9.8% TX-150, and 0.23% NaCl. The relative permittivity of the fat phantom is approximately 8 to 9. The Lagendijk published conductivity is 0.04 S/m.

Figure 3B:
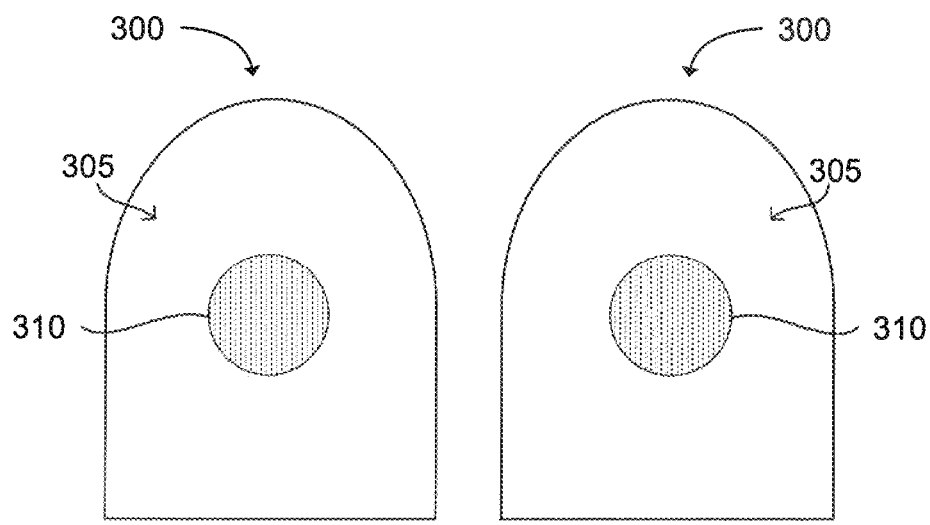
FIG. 3b is a top view of the test phantom material of FIG. 3a that is split in half to measure a temperature of the phantom material in accordance with an embodiment of the present invention.

The phantom material, as shown in FIG. 3b, can be split in two so that it can be heated and then immediately opened for test and measurement. This is done to provide an accurate measurement of an internal temperature of the simulated fatty tissue 305 and cancerous tumor 310 within the phantom breast 300.

The wax phantom and the flour phantom were both tested under a variety of conditions. In one test of the wax phantom, four power channels were respectively coupled to the four dipole antennas 30, 31, 33 and 35, as illustrated in FIG. 2. The wax phantom was placed into the aperture 26. The four power channels were set at a relative phase of zero degrees for dipoles 30 and 35 and ninety degrees for dipoles 31 and 33, resulting in a circularly polarized field, as previously discussed. The tests were done with a bolus medium comprised of either deionized water, mineral oil, or an equivalent. The entire volume 24 of the test device can be filled with the bolus medium. Alternatively, the fluid can be confined to an area around the surface of the breast 32. In one test, the split in the phantom was oriented to be centered on dipoles 30 and 35 to allow maximum heating from the dipoles. The two halves of the phantom were separated by a thin sheet of plastic (saran wrap) to reduce evaporative cooling when the phantom was split. A similar setup was used in testing the flour phantom.

The output of the dipole antennas 30, 31, 33 and 35 can be tuned based on the type of bolus used. For example, for an oil bolus the antennas were tuned to be substantially impedance matched with the oil medium. A tuning circuit was adjusted using a Bazooka balun. A Bazooka balun is a quarter wave length of coaxial line that has the outer conductor cut away along a strip on opposite sides forming a quarter wave length of parallel line and at the tip having the center conductor short to one of the outer conductor sides to form one of the two active connection points for a balanced line. Doing this, the impedance match at 915 MHz was between 10 dB to 30 dB return loss. The tuning match was achieved by adding a capacitive shunt at a feed point of the tuning circuit.

Through testing, it was determined that use of an oil bolus with a dielectric between 2.5 and approximately 4 provided less heat absorption by the bolus compared to the use of the deionized water bolus. The lower dielectric value of the oil bolus compared with the deionized water bolus substantially reduces higher order energy modes from propagating in the bolus space. However, a water bolus may still be used if additional methods are used to prevent the higher order modes in the water. Reducing the higher order modes in the water may be accomplished using artificial dielectric modification methods such as low dielectric vanes or sheets that are cross polarized with the dipoles to present perpendicular dielectric boundaries to the electric fields in the radio frequency electromagnetic fields used to selectively heat a tumor. Higher fill factors of the breast relative to the bolus size can also reduce higher order modes. The fluid in the bolus can be circulated to provide additional cooling to the surface of the breast with which the bolus is in contact.

Figure 4:
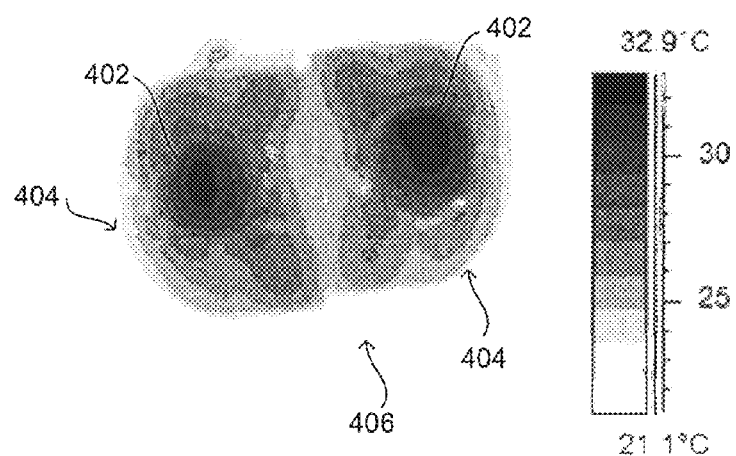
FIG. 4 is an infrared photo of a phantom breast immediately after being selectively heated, the photo showing the temperature variations for the tumor tissue and normal breast tissue representations.

An infrared camera was used to record the temperature of the split phantom after it was selectively heated as previously described. The infrared image shown in FIG. 4 shows the tumor center 402 increased in temperature from a room temperature of about 24 degrees Celsius to a temperature of 32.2 degrees Celsius for a change in temperature of 8.2 degrees Celsius. The phantom surface 404 increased from room temperature to about 27 degrees Celsius. The oil bolus fluid 406 was recorded with a maximum temperature of approximately 25.1 degrees Celsius. The image shown in FIG. 4 shows selective heating of a simulated tumor 402 in a breast equivalent phantom.

The actual amount of power that is sent to each antenna and the length of the exposure can be controlled to achieve desired results. For hyperthermia and thermal therapy systems it is common to monitor target tissue temperature during heating by invasive and at times non-invasive thermometry to provide a control parameter for power levels. In some cases, lower power can be applied for a longer period. For example, 30 watts of power may be sent to each antenna for a period of six or more minutes. Power can be reduced as needed to maintain the desired temperature for a prescribed period that may be as long as 60 minutes. In other cases, it may be desirable to apply more than 50 watts per channel for a relatively shorter period. For example, 100 watts of power may be sent to each antenna for a period of less than two minutes to reach a therapeutic temperature level which will vary with differing blood-flow. In other embodiments, different amounts of power may be sent to each antenna in the array. For example, when a tumor is not centered within the breast, it may be desirable to provide different power ratios to provide substantially even heating on each side of the tumor. The ability to monitor temperature of such a tumor and control the power to maintain a target temperature level is a common element in such applications. Typically temperature is set to over 40 degrees Celsius and maintained for up to 60 minutes. Higher temperatures such as 60 degrees Celsius need only be maintained for less than a few minutes.

Figure 5:
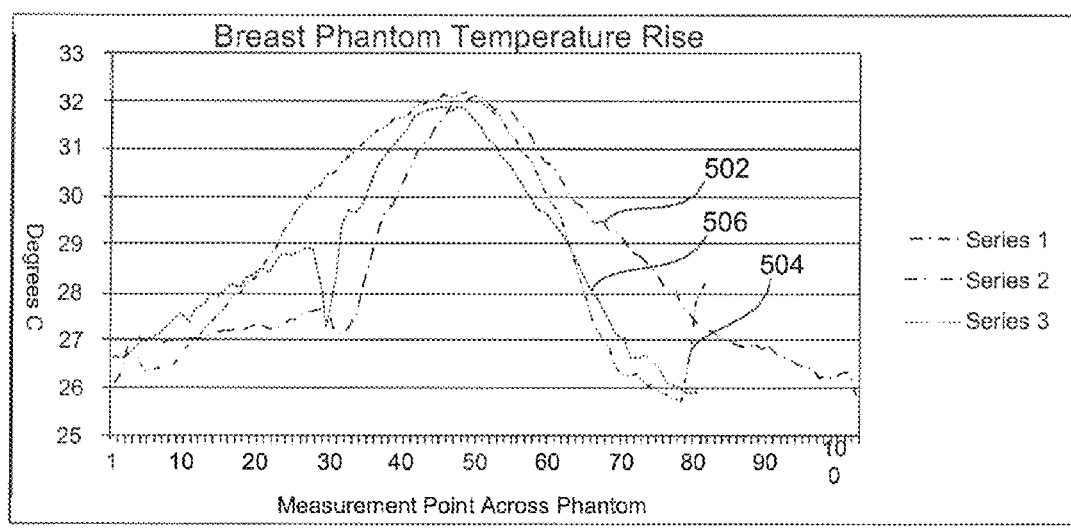
FIG. 5 is a chart showing a plurality of temperature measurements made across a phantom breast after it has been selectively heated.

FIG. 5 illustrates a diagram showing a plot of the temperature across the breast phantom. The Series 1 line 502 represents 100 temperature points taken across the wax phantom from left to right passing through the center of the tumor model. The Series 2 line 504 represents 100 temperature points taken across the phantom from back to front through the center of the tumor model. The Series 3 line 506 represents 100 temperature points taken in a diagonal from the left base of the breast phantom passing through the central tumor model and ending at the frontal side surface of the wax breast phantom. Each of the series lines show that the temperature dramatically increases at a center of the phantom, where the tumor model is located, thereby showing selective heating of a tumor in the breast equivalent phantom.

Additional testing was performed, with each test showing a significant heating of the tumor relative to the surrounding tissue. The following table summarizes the temperature change of the tumor material in the paraffin phantom and the surface temperature of the phantom as a result of short term heating experiments to measure where the power is being primarily absorbed.

| Tests | Tumor Max Temp. Change | Surface Max Temp Change |
|---|---|---|
| 1 | 8.2° C. | 3.0° C. |
| 2 | 11.8° C. | 3.9° C. |
| 3 | 10.7° C. | 5.4° C. |
| 4 | 8.8° C. | 2.7° C. |

The average ratio from these tests of the tumor maximum temperature rise versus the average maximum temperature rise on the phantom surface is 9.875/3.75=2.63. Thus, a tumor located in a fatty breast tissue can be selectively heated using radio frequency waves when the tumor has a diameter that is around $\frac{1}{3}^{rd}$ of the wavelength of a radio frequency electromagnetic field in the fatty tissue. In other words, the wavelength of the radio frequency waves in the fatty breast tissue will be about three times a width of the tumor for optimal resonant heating. Of course, resonant heating can still be attained within a range of wavelengths. The wavelength of the radio frequency waves in the fatty tissue may be +/−about 25% of the optimal length, or in other words about 3.75 times a diameter of the tumor to about 2.25 times a diameter of the tumor. Alternatively, a single frequency such as 915 MHz can be used to provide resonant heating of tumors. The tumor can optimally be about $\frac{1}{3}$ of the wavelength of the radio frequency waves in the fatty tissue. At 915 MHz, the wavelength in the fatty tissue is approximately 14 cm. Thus, a tumor within a range of 25% from the optimal size will have a diameter of about 3.5 cm to 5.25 cm. Some resonant heating may be attained for tumors within a 50% range from the optimal size of 4.6 cm. Thus, selective heating can be accomplished for a tumor or another deposit such as a cyst, or high conductivity implant having a diameter of about 2.3 cm to over 7 cm, with an increased amount of selective heating when the tumor has a size of about 4.5 cm. Additional preparation of a deposit can increase selective heating.

Figure 6:
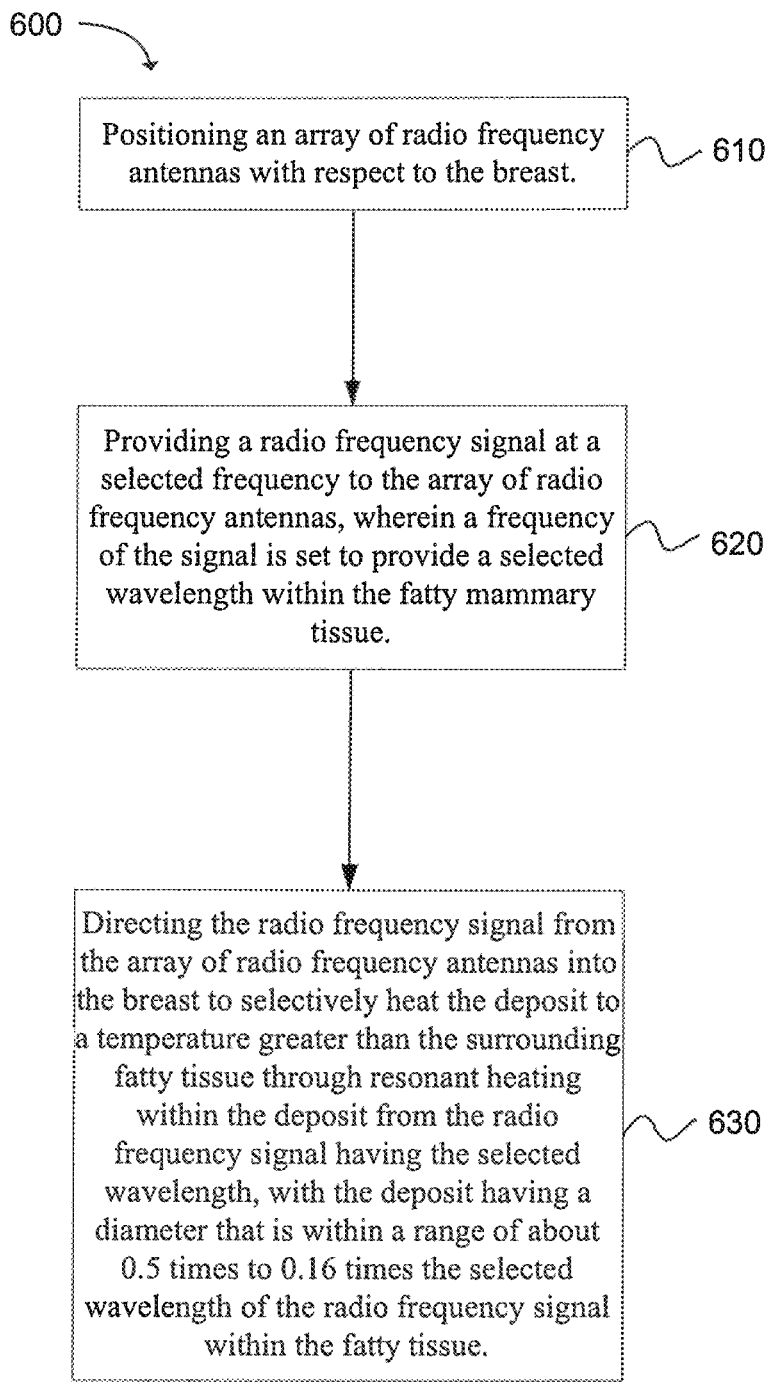
FIG. 6 is a flow chart depicting a method of selectively heating a deposit in a breast in accordance with an embodiment of the present invention.

In another embodiment, a method 600 of selectively heating a deposit in a breast having fatty mammary tissue surrounding the deposit is disclosed, as depicted in the flow chart in FIG. 6. The deposit can be any non-native body within the breast, such as a cancerous tumor, cyst, or high conductivity implant. The method includes the operation of positioning 610 an array of radio frequency antennas with respect to the breast. The antennas in the array can be positioned around the breast to provide substantially even heating of the deposit within the breast. In one embodiment, at least one antenna in the array can be positioned to emit waves perpendicular to another antenna in the array and 90 degrees out of phase to provide substantially circular polarization of the electromagnetic field in the breast and deposit. In one embodiment, the array can be comprised of two antennas that are substantially in phase and two antennas that are positioned to direct orthogonal waves that are about 90 degrees out of phase with the first two antennas to provide the circularly polarized electromagnetic field. Additional antennas may also be used, such as antennas located below the breast and tumor.

The method 600 further includes the operation of directing 630 the radio frequency signal from the array of radio frequency antennas into the breast to selectively heat the deposit to a temperature greater than the surrounding fatty tissue through resonant heating within the deposit from the radio frequency signal having the selected wavelength. The deposit can have a diameter that is within a range of about 0.5 times to 0.16 times the selected wavelength of the radio frequency signal within the fatty tissue. A radio frequency signal generator can be used to provide 620 the radio frequency signal at the selected frequency to the array of radio frequency antennas.

In one embodiment, a radio frequency signal having a frequency of 915 MHz may be used. Substantially optimal resonant heating can be obtained when a deposit such as a cancerous tumor, cyst, or high conductivity implant has a diameter that is approximately ⅓ of the wavelength of the signal in the fatty breast tissue.

To increase the resonant heating effect to the tumor, the conductivity or dielectric constant of the tumor may be changed by injecting material into the tumor. For example, material such as a saline solution may be injected to increase the conductivity or dielectric constant of the tumor relative to the fatty breast tissue. The saline solution may also act as a carrier for additional material, such as carbon nanotubes or other types of material that can increase the conductivity or dielectric constant of the tumor. The carbon nanotubes or other material can be injected into the tumor to substantially increase its conductivity, thereby increasing the selective heating of the tumor relative to the surrounding tissue to a level greater than the average 2.63 times increase shown in the test data above.

The heating described can also be used to selectively heat a breast tumor to enhance tumor therapeutic affects by other cancer treatments such as radiation or chemotherapy (such as selective heat release of liposome encapsulated chemotherapy), or both. As one non-limiting example of a combined therapy/hyperthermia treatment, a traditional cancer therapy (e.g., chemotherapy and/or radiation) is given to a patient and followed by a computed tomography (CT) scan or other appropriate scanning technique to locate the precise location of the tumor within the tissue. The hyperthermia treatment is then given as described hereinabove. After the final hyperthermia treatment is given, a radiation oncologist measures the tumor shrinkage by any suitable means, and recommends the least invasive type of surgery to remove the tumor. Surgery is followed by additional therapy and hyperthermia treatment, if one or both procedures are indicated at this stage, to kill any undetected cancer cells in the tissue.

The present invention is not limited to selectively heating tumors or other deposits of body tissue needing heat treatment. Other types of deposits within a protruding body portion can also be selectively heated using a proper wavelength of radio frequency waves to provide resonant heating of the deposit within the body portion. For example, after a lumpectomy is performed to remove a tumor, a balloon like device can be implanted into the area where the tumor was located. The balloon like device may be inflated and used in additional radiation or heat treatments. In one embodiment, the balloon can be inflated with a selected material having a desired conductivity and dielectric constant relative to the surrounding fatty breast tissue to enable the material in the balloon to be optimally selectively heated, at least in part through resonant heating, using radio frequency waves, as previously discussed. In one embodiment, an implantable device such as a Mammosite® device can be used to selectively heat an area within the breast where a tumor was previously removed. Alternatively, the balloon and material may be inserted prior to the tumor's removal and used to apply heat to the tumor.

An example of the above is the use of the mentioned Mammosite® device or similar device. A common practice for treatment for breast tumors which are localized in the breast and not overly large and have no lymph node involvement, is to do a partial breast resection which is called a lumpectomy. This is a minimally invasive surgery that removes the known area of breast tumor involvement leaving a cavity in the breast where the tumor resided. This procedure leaves the breast intact and is now a primary method to treat breast cancer primary tumors when the breast tumor is not overly large. Very large or advanced breast tumors generally require radical surgical removal of the breast to attempt to remove all cancerous tissues. When a lumpectomy is performed is it generally followed by additional treatment using radiation therapy and/or chemotherapy to attempt to destroy any small tumor tissues or cells that may have either been left over after the lumpectomy or may have been beyond the surgical margins of the partial breast resection. Generally, it is desirable to treat cells within five to ten mm of the surgical margin. A common way to do radiation therapy of the tissue surrounding a post lumpectomy cavity created by the surgery is to place a special catheter into the breast that has a thin walled balloon that is positioned in the cavity and that is then inflated with saline fluid (salt water) to fill the cavity with the saline fluid filled balloon. This special catheter is commonly called a Mammosite® device as developed by Proxima Therapeutics, Inc., but now available from a number of sources. This special catheter has a passage that is used to fill and drain the balloon when the balloon is positioned in the cavity. It also has one or more other passages that permit the insertion and removal of a high dose radiation (HDR) emitter in the device aligned with the inside of the balloon which radiates ionizing radiation through the balloon into the tissues surrounding the balloon, i.e., the tissue surrounding the cavity and forming the perimeter of the cavity.

However, the level of radiation that can be safely applied to a patient is limited due to both short term and long term toxicity to the patient. To reduce as much as possible the amount of radiation applied, there is a need to increase the effectiveness of the radiation that is applied. As indicated above, it has been found that hyperthermia, heating the radiated tissue to between 41 degrees C. and 45 degrees C. increases the effectiveness of radiation treatments. The heating can be done after the radiation treatment, before the radiation treatment, or during the radiation treatment. Alternatively, with an increased temperature treatment of the tissue surrounding the cavity wherein temperature in excess of 45 degrees C. are reached, usually temperatures in excess of 50 degrees C., radiation therapy may not even be necessary as the increased heating kills the target cells by heat coagulation or ablation of the cells.

Figure 7:
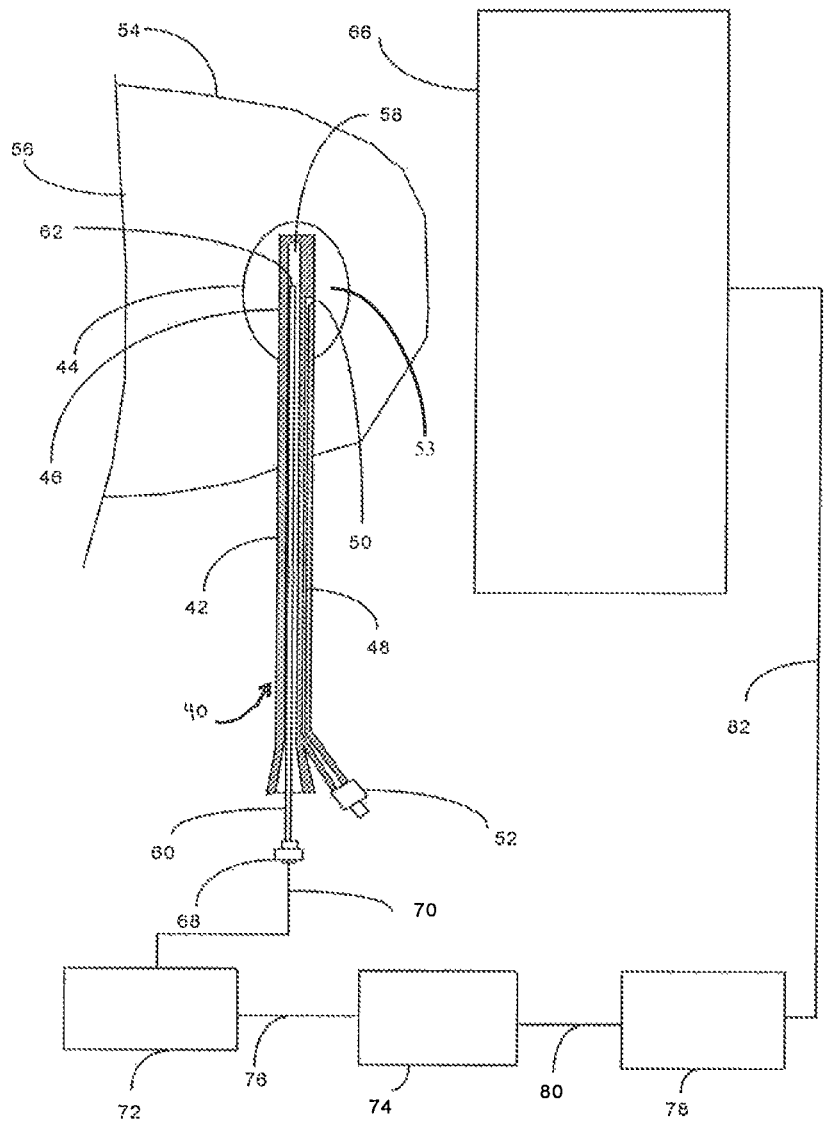
FIG. 7 is a schematic showing of a system for heating an inserted deposit of material in a breast.

Referring to FIG. 7, a Mammosite® device is shown generally as 40 and comprises a catheter device 42 with a balloon 44 positioned around the distal end portion 46 of the catheter device 42. A passage 48 extends from an opening 50 within the balloon 44 to a fluid valve 52 adapted to be connected to a source of inflating fluid. Thus, with fluid valve 52 open, a fluid 53 can be forced through passage 48 to fill balloon 44. When balloon 44 is filled to the desired extent to fill the cavity, fluid valve 52 is closed to maintain the fluid 53 in balloon 44.

The Mammosite® device 40 is shown with its distal end portion positioned within a breast 54 extending from a women's chest wall 56. Usually this will position the balloon in a cavity in the breast formed by the removal of a tumor from the breast by a lumpectomy. As indicated above, the Mammosite® device is usually used to apply radiation to the walls of the cavity and the tissue surrounding the cavity. To accomplish this, the catheter device 42 includes an insertion passage 58, here shown as a central passage, into which a radioactive seed, wire, or particle, not shown, is inserted to provide the radiation source for the radiation therapy which can be at times scanned to properly distribute the intended radiation dose to the tissue. When radiation is not being applied, insertion passage 58 is empty. This allows a temperature sensor probe 60 with a temperature sensor 62 at its distal end to be placed in insertion passage 58. With temperature sensor 62 positioned along insertion passage 58 so as to be within balloon 44, temperature sensor 62 can measure, through the walls of the catheter device 42, the approximate temperature of the fluid 53 inside the balloon. The temperature of the surface of the balloon will also approximate the temperature of the fluid 53 within the balloon 44. Where the temperature of the fluid 53 in balloon 44 is higher than the temperature of the breast tissue surrounding balloon 44 (i.e., the tissue forming the walls of the cavity), balloon 44 will heat the surrounding breast tissue. Thus, by heating the fluid 53 in balloon 44, the surrounding breast tissue can be heated. As indicated above, it is desirable to heat such surrounding breast tissue in conjunction with radiation therapy or chemotherapy to increase its effectiveness, or to use heating of the breast tissue alone to coagulate or ablate such tissue. Also, as indicated, the desired depth of treatment of the tissue around the cavity is between about 5 and 10 mm. Such depth can be easily heated by the heated balloon.

Figure 8:
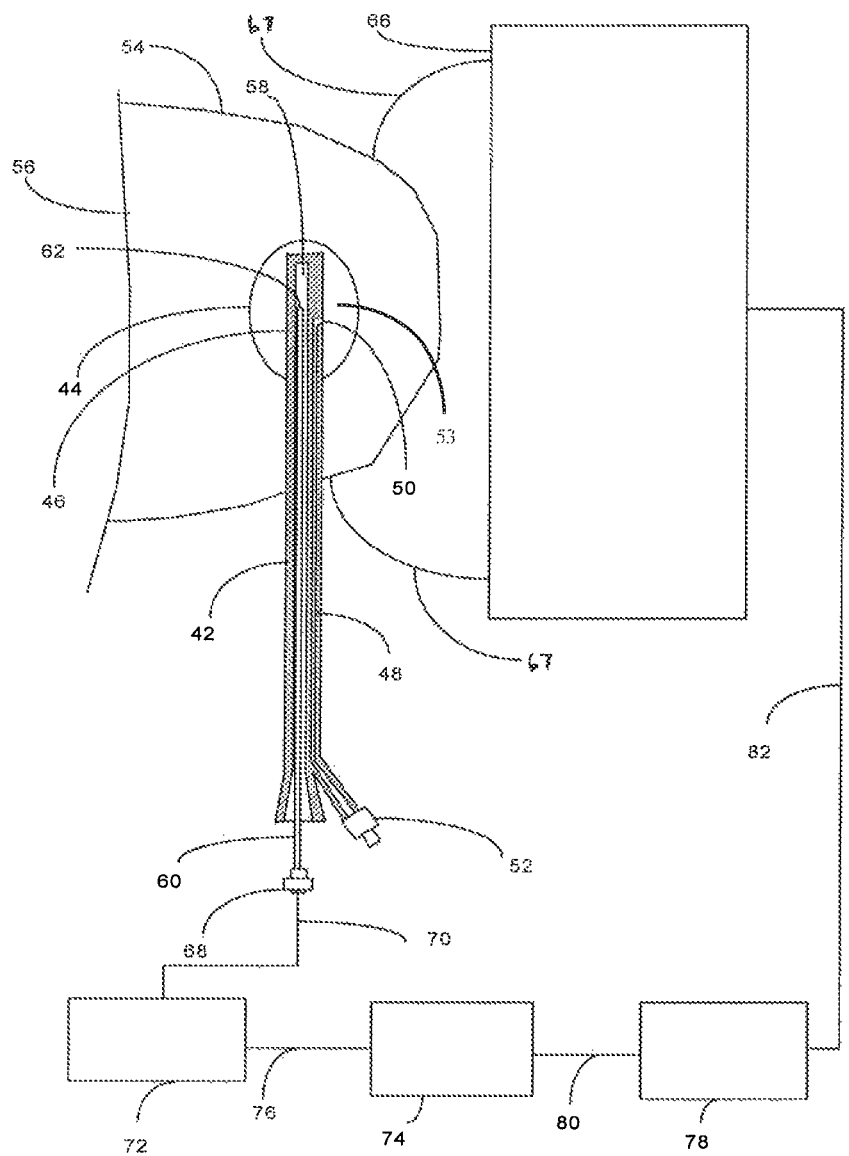
FIG. 8 is a schematic showing of a system for heating an inserted deposit of material in a breast similar to that of FIG. 7, but showing a bolus positioned between the microwave applicator and the breast.

In accordance with the invention, the balloon 44 can be inflated with a selected material 53 having a desired conductivity and dielectric constant relative to the surrounding fatty breast tissue to enable the material 53 in the balloon to be optimally selectively heated using radio frequency waves. Further, the inflated balloon can be sized so that it, in conjunction with the frequency of the radio frequency waves being used, is selectively heated through resonant heating. In use, balloon 44 is filled with the selected material 53, such as a saline solution, and the breast is subjected to microwave radiation from a microwave radiation source, indicated schematically in FIG. 7 as 66, in a manner as previously described herein. A dielectric filled bolus 67, FIG. 8, can be provided between the microwave source 66 and the breast 54 to be treated. Thus, a breast to be treated can be positioned in the apparatus of FIGS. 1 and 2 for treatment. Upon application of microwave energy to the breast, the fluid 53 in balloon 44 will be selectively heated, at least in part by resonant heating, to a higher temperature than the breast tissue surrounding the balloon 44 and heat will be conducted from the balloon to the surrounding tissue to heat the surrounding tissue. In order to control the temperature of the fluid 53 in balloon 44, temperature sensing probe 60 is inserted into catheter insertion passage 58 to position temperature sensor 62 in alignment with the inside of balloon 44 so temperature sensor 62 can measure the approximate temperature of the fluid 53 in balloon 44. Temperature sensor 62 is connected through temperature sensor connector 68 and cable 70 to a temperature sensing circuit 72, connected to system controller 74 through cable 76. System controller 74 is connected to microwave generator 78 through cable 80. In this manner, the system controller can control the microwave energy sent through microwave supply cable 82 to be applied to the breast to control the temperature of the fluid 53 in balloon 44 at the desired temperature for the intended treatment time. The duration of time as well as the temperature establishes the thermal dose delivered to the surrounding tissue. The controller monitors the time of the treatment during which the balloon fluid 53 is at the therapeutic temperatures. Generally, the insertion passage 58 will not be of a size to accommodate both the high dose radiation emitter and the temperature sensing probe at the same time so the heating microwave radiation will be applied either before or after the application of the radiation when the HDR emitter is removed from the catheter insertion passage 58 and the temperature sensing probe can be inserted into the catheter insertion passage 58.

Figure 9:
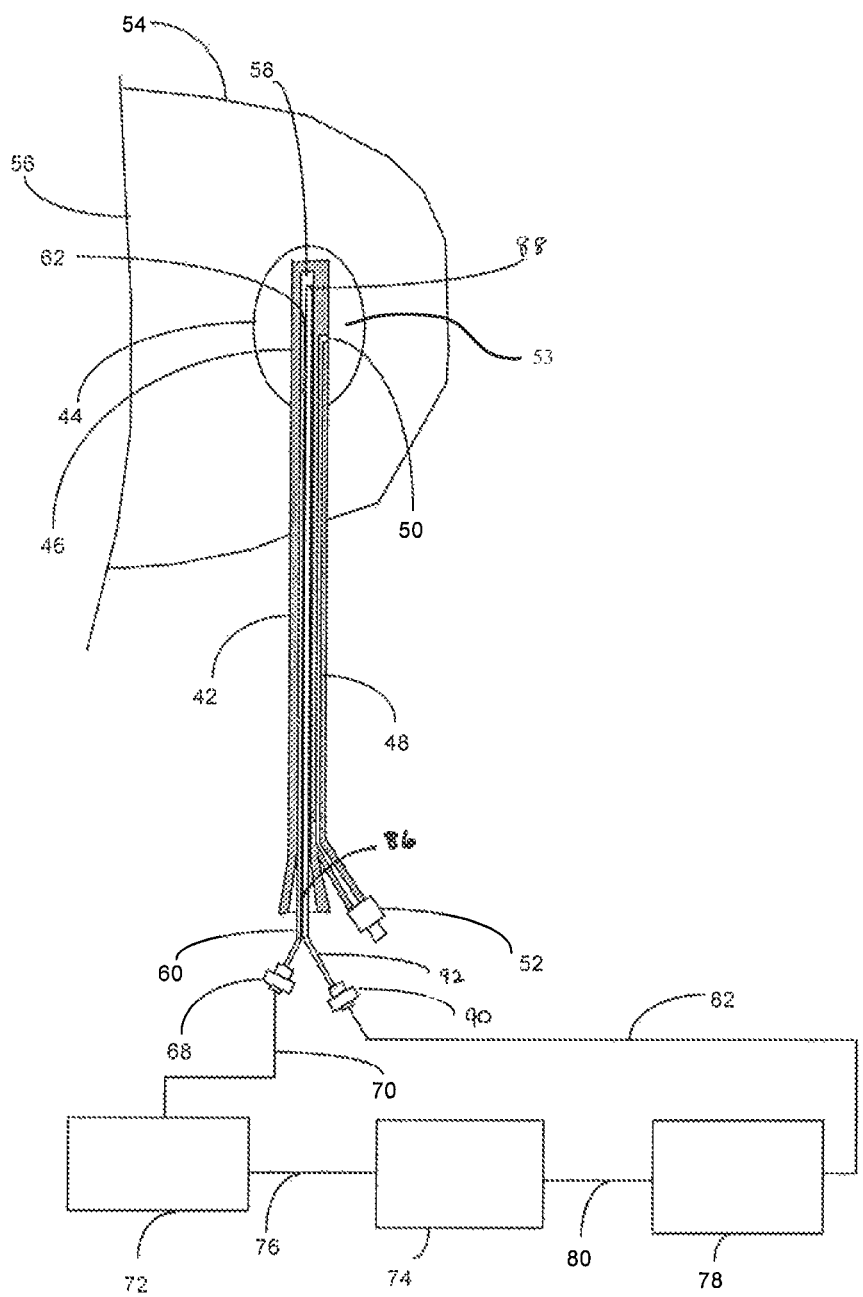
FIG. 9 is a schematic showing of an alternate system for heating an inserted deposit of material in a breast with the microwave applicator positioned within the inserted deposit.

Alternately, as shown in FIG. 9, rather than placing the breast in a device such as shown in FIGS. 1 and 2 to apply microwave energy to the breast and the inflated balloon of the Mammosite® type device from outside of the breast, when using a Mammosite® type device, a microwave applicator 86 having a radiating microwave antenna in the distal portion 88 thereof may be inserted into the insertion passage 58 of the Mammosite® type device so that the microwave emitting antenna is located within the balloon 44. In such case, microwave supply cable 82 from the microwave generator 78 is connected through cable connector 90 and applicator cable 92 to the microwave antenna in distal portion 88 of microwave applicator 86. When heating of the balloon is desired, microwave energy is supplied by the microwave generator to the antenna positioned in the catheter passage in the balloon to be radiated outwardly from the passage aligned with the center of the balloon through the material 53 in the balloon and into the breast surrounding the balloon. Here again, the balloon 44 can be sized and be inflated with a selected material 53 having a desired conductivity and dielectric constant relative to the surrounding fatty breast tissue to enable the material 53 in the balloon to be optimally selectively heated using radio frequency waves, including being selectively heated through resonant heating. The temperature sensor 62 measures the approximate temperature of the material 53 in the balloon and the microwave power applied to the applicator is controlled to maintain the material 53 in the balloon at a desired temperature. Again, the insertion passage 58 will not generally be of a size to accommodate both the high dose radiation emitter and the microwave applicator and temperature sensing probe so the heating microwave radiation will be applied either before or after the application of the radiation when the microwave applicator and temperature sensing probe can be inserted into the catheter passage. Rather than a separate microwave applicator 86 and temperature sensing probe 60 both being inserted together in the insertion passage 58, a temperature sensor can be built into the microwave applicator.

In either heating situation, the balloon will be sized and the amount of material placed in the balloon to inflate the balloon will be controlled to provide an inflated balloon of a diameter of about one third the wavelength of the radio frequency signal within the fatty breast tissue surrounding the balloon, plus or minus about twenty five percent of the one third dimension. This equates to the balloon being within the range of about 0.5 times to about 0.16 times the wavelength of the radio frequency signal within the fatty breast tissue surrounding the balloon. However, since the size to which the balloon can be inflated is somewhat discretionary, the best results will be achieved when the inflation puts a diameter of the balloon at the one third the wavelength of the radio frequency signal within the fatty breast tissue. With a frequency of 915 MHz, a diameter of the balloon should be about 4.5 cm. In addition, while a saline solution has been found satisfactory for inflating the balloon, the material inflating the balloon can be selected to provide a desired dielectric constant and conductivity value to provide maximum resonant heating. Where radiation is provided through the balloon, the material inflating the balloon has to be compatible with radiation application.

To show the viability of heating a fluid in the balloon of a Mammosite® type device and using the heated balloon for providing heat treatment of the tissue surrounding the balloon, a fat equivalent breast phantom was prepared as previously indicated for the flour breast phantom: flour 500 parts, cooking oil 250 parts, and 2% saline 50 parts by weight. A cavity was formed to enable the Mammosite® device to be filled with saline and placed in the center of the breast tissue phantom. The balloon was filled with about 40 cc of saline. For each test, the breast and chest wall phantom started at room temperature of about 22° C. In Test 1, an FDA approved BSD-500 hyperthermia system with MA-100 applicator was used to apply microwave power with about a 3 mm minimum air gap over the breast phantom. The Mammosite® type device was placed in the approximate center of the breast phantom. This experiment was repeated a day later as Test 2.

An additional experiment, Test 3, was done using an inserted microwave applicator in the open silicone tube of the Mammosite® type device. A normal inner nylon catheter had been removed for this test.

In each experiment, microwave compatible thermistor temperature sensors of the BSD-500 system were used to measure and control the temperature of the saline solution filling the balloon of the Mammosite® type device. In addition, other sensors were placed at various positions in the phantom during treatment to monitor heating of other tissues areas. A thermocouple probe was also used post treatment for Test 2 and Test 3 to sample temperature in the breast phantom at various radial depth positions. Also, liquid crystal thermographic temperature sheet material was used to view the temperature distribution of the phantom along a central split line after Test 2 and Test 3.

The testing showed that very rapid heating occurred within the saline solution of the Mammosite® type device. The microwave power was controlled to maintain the temperature measured by a temperature probe inserted in the center lumen of the Mammosite® type device at 43 degrees C. for much of the test time. Another sensor was placed first in the 42 degree thermal well and at 13 minutes and at 15 minutes in contact with the balloon and the split phantom was opened for a period when the rf power was turned off. The power was turned on again at about 17 minutes when the other probe was placed at about 3.3 mm from the balloon.

Test 1 demonstrated that selective heating occurs in the Mammosite® type device fluid when using an external microwave radiator such as the BSD MA-100 applicator. The temperature rise rate of the balloon was about 3.3° C./minutes with an applied power of 100 watts. The average power to maintain a temperature of about 43° C. was ten to fifteen watts.

Test 2 used the same initial power of 100 watts to heat the phantom and the saline filled balloon. A temperature sensing probe was centered in the balloon lumen and the systems control was set to control the balloon temperature at 50° C. A second temperature sensing probe was placed about 3 mm radial depth to the balloon. A third temperature sensing probe was placed between the breast phantom and the muscle phantom simulating the chest wall. A fourth temperature sensing probe was placed on the surface of the breast phantom in the center. The balloon temperature rapidly reached 50° C. at a rate of 3.3° C./minute at 100 watts. Once the temperature reached this level, the system automatically controlled power to maintain this temperature in the central lumen of the Mammosite® type device, i.e., in the center of the balloon. The probe that was 3 mm away also rapidly increased but with a time delay that indicated that much of the heating there was due to conduction of heat from the balloon. The heating of the tip of the breast phantom was steadily increasing indicating that it also was primarily due to heat conduction. The chest wall probe responded rather quickly in its rate of rise indicating that much of its heating was due to local microwave absorption. The tissue over the surface of the balloon to the tip of the breast phantom was about 1.5 cm. The distance between the balloon and the chest wall phantom was also about 1.5 cm. The rate of heating along the chest wall was only 1° C./minute and on the tip surface of the breast phantom was 0.6° C./minute. The rate of rise of the 3 mm probe was 2.6° C./minute during the heat up period and was 0.2° C./minute once the power started to be controlled to maintain the 50° C. on the balloon. This implies there was about 10 times more heating at the 3 mm depth that was due to direct power absorption than was due to conductive heat flow. The average power required to maintain the 50° C. level for the balloon temperature ranged from 18 to 22 watts.

The temperature measurements showed that the balloon heated at a rate that was 3.3 times greater than the chest wall phantom. This demonstrates that very selective heating of the balloon was possible, but there was some significant direct power absorption by fatty tissues close to the balloon. The steady heating rate at the tip of the breast phantom both before and after the significant drop in RF power showed that region was heated mostly by conductive heat transfer. Since the initial phantom and saline balloon temperature started at 22° C., the 3 mm radial depth sensor temperature changed by 21° C. (75% change) when the balloon temperature changed by 28° C. Thus, it can be implied that when this is done in a patient that has tissue temperatures of about 37° C. at the start and the balloon is heated to 48° C., the 3 mm depth tissues would increase by about 8.3° C. and initially reach a temperature of 45.3° C. This suggests that the 6 mm depth change may initially be about half of the balloon temperature change and reach 42.5° C. initially when the balloon reaches 48° C. This is well within the therapeutic heating range to significantly boost the radiation dose. Probing the tissue with a thermocouple after the session showed that tissues that were about 8 to 10 mm away from the balloon reached about 43° C. for a 42% temperature change of that of the balloon. This suggests that therapeutic temperatures would be reached above 41.6° C. at a depth of about 8 to 10 mm for a balloon temperature of 48° C. if the initial temperature of a patient was 37° C.

Liquid crystal pictures of the split phantom of Test 2 showed a rather symmetrical heating band uniformly oriented around the balloon region showing the 30° C. or greater temperature depth was as large as about 14 mm. The temperature change range of the liquid sheet used was 30 to 35° C. This demonstrated that by the end of this test the temperature change to that depth was about 28% of that of the balloon.

Test 3 was a test using an inserted antenna in the lumen of the silicon Mammosite® type device. This testing was similar to the test 2 testing. Only one probe was next to the balloon. This test raised the balloon temperature to 48° C. at a rate of 2.7° C./minute using 32 watts of power. The average power needed to maintain this temperature in the balloon ranged from 8 to 10 watts. It was noted that with the split phantom view of the liquid crystal sheet, the heating pattern was not as symmetrical as when using the MA-100 external applicator. The heating seemed to be weaker at the chest wall side of the breast and the tip of the Mammosite® type device as compared to between the balloon and the tip of the breast and the insertion end of the Mammosite® type device. It was not clear what the cause of this was. The thermocouple sensor indicated that at about 6 mm away from the balloon, near the chest wall, the temperature was about 31° C. and about 35° C. at that distance toward the breast tip surface. The asymmetry cause was not determined. It could have been a difference of the tightness of the balloon at the upper regions to the cavity or poor contact between the split phantom surfaces at the chest wall region. Since Test 2 showed that there was a rather direct relationship to the heating rate of the balloon and the close probe, there may not have been as much RF energy transferred to the lower phantom portions of the cavity due to an air gap at the bottom of the cavity. The results of Test 3 showed that placement of the microwave antenna in the catheter in the balloon did not perform as well as heating in the other tests using the external microwave antenna applicator.

The tests showed that the Mammosite® type device can be selectively heated using microwave energy. The above described tests used standard saline solution in the balloon. Standard saline solution is typically a concentration of about 0.9% salt in water. The dielectric of mammary fatty tissue is 5.4 and conductivity is 0.050 S/m at 915 MHz. The dielectric of standard saline is 75 and conductivity is 1.7 S/m. However, various other fluids may be used with either higher dielectric and or higher conductivity than the mammary tissue or normal saline. Further, the enhanced resonant heating of the saline occurs with either linear or circular polarization. The above tests using the Mammosite® type device were conducted with linear polarization. Circular polarization would be expected to provide further improvement as circular polarization would spread the fields in the surrounding tissues more uniformly, while keeping the selective heating of the stagnant saline fluid to impart heat therapy to the surrounding mammary tissues.

While the use of a deposit inserted into tissue adjacent tissue to be heat treated has been described as a balloon, this is merely an example. The inflatable balloon has the advantage that it can be inserted into and positioned in the tissue in a deflated condition, and, when in position, can be inflated to a desired size. However, various other forms of flexible or rigid deposits can be inserted into the tissue in various manners, such as surgically, to be adjacent tissue to be treated and surrounded by tissue not in need of treatment. Further, while the tissue surrounding the deposit in the above example is fatty mammary breast tissue which has low water content in comparison with the high water content of the balloon forming the deposit, a similar deposit can be used in other body locations in higher water content tissue surrounding the deposit. All that is needed is that the deposit material have a higher dielectric constant and/or a higher conductivity than the tissue which surrounds the deposit, and that the size of the deposit is within the range of about 0.5 times to about 0.16 times the wavelength of the radio frequency signal within the tissue surrounding the deposit. An example was given above where a deposit of between approximately 5 to 11 cm in diameter, optimal about 7 to 8.6 cm in diameter, surrounded by high water content tissue such as muscle tissue, can be heated by resonant heating using a radio frequency signal of 120 MHz wherein the wavelength of the radio frequency signal in the surrounding high water content tissue is between approximately 22 to 27 cm. With the use of an inserted deposit, the deposit material can be selected so as to provide the higher dielectric constant and/or a higher conductivity than that of the tissue which surrounds the deposit so as to enable the resonant heating to take place.

It can be appreciated that the embodiments disclosed hereinabove have potential applications outside the immediate scope of cancer therapy, such as cellular necrosis, chemical reaction kinetics, and catalysis. It will also be understood only examples of the invention have been shown and described and that various details of the invention may be changed without departing from the scope of the invention. Furthermore, the foregoing description is for the purpose of illustration only, and not for the purpose of limitation.

What is claimed is:

1. An apparatus for providing hyperthermia treatments to a breast having fatty mammary tissue surrounding tissue in need of said hyperthermia treatment, said fatty mammary tissue having a dielectric constant and a conductivity, comprising:

a cavity for receiving the breast therein;

a first radio frequency antenna operable to direct a radio frequency signal at a selected frequency into the breast received in the cavity, said radio frequency signal having a wavelength within the fatty mammary tissue; and a deposit adapted to be positioned in the fatty mammary tissue of the breast adjacent the tissue in need of said hyperthermia treatment, said deposit having at least one of a dielectric constant and conductivity greater than the dielectric constant and conductivity of the fatty mammary tissue and having a diameter within a range of about 0.5 times to 0.16 times the wavelength of the radio frequency signal within the fatty mammary tissue whereby the deposit, when positioned in the fatty mammary tissue adjacent the tissue in need of said hyperthermia treatment, will be heated, at least partially by resonant heating, by the radio frequency signal, the heated deposit then supplying heat for said hyperthermia treatment to the tissue adjacent the deposit.

2. The apparatus of claim 1, wherein the deposit includes a material having at least one of a dielectric constant and a conductivity greater than that of the fatty mammary tissue surrounding the deposit.

3. The apparatus of claim 1, wherein the deposit includes an inflatable balloon adapted to be inflated with a material having at least one of a dielectric constant and a conductivity greater than that of the mammary tissue surrounding the deposit.

4. The apparatus of claim 3, wherein the inflatable balloon is positioned around a portion of a catheter adapted to be inserted into the breast to position the inflatable balloon adjacent the tissue to be treated.

5. The apparatus of claim 4, wherein the material is an inflation material, wherein the catheter includes an inflation passage therein through which the inflation material is passed to inflate the inflatable balloon after it is positioned adjacent the tissue to be treated.

6. The apparatus of claim 5, wherein the catheter includes a passage therein extending along the catheter to a position aligned with the inside of the inflatable balloon and adapted to receive a temperature measuring probe therein so as to place a temperature sensor in position to measure the approximate temperature of the inflation material in the balloon.

7. The apparatus of claim 5, wherein the catheter includes a passage therein extending along the catheter to a position aligned with the inside of the inflatable balloon and adapted to alternately receive a temperature measuring probe therein so as to place a temperature sensor in position to measure the approximate temperature of the inflation material in the balloon and a high dose radiation emitter.

8. The apparatus of claim 1, wherein the selected frequency of the radio frequency signal is about 915 MHz.

9. The apparatus of claim 1, wherein the deposit has a diameter in a range of about 2.3 to 7 centimeters.

10. The apparatus of claim 1, wherein the radio frequency antenna is an antenna array operable to direct a circularly polarized radio frequency electromagnetic field into the breast.

11. Apparatus for providing heat treatment to living tissue in need of such heat treatment and surrounded by living tissue not in need of such heat treatment, said living tissue not in need of such heat treatment having a dielectric constant and a conductivity, comprising:
   a deposit of material in a form to be positioned in the living tissue adjacent the tissue in need of heat treatment, said deposit of material having a diameter, dielectric constant, and conductivity; and
   a source of radio frequency radiation adapted to direct the radio frequency radiation through said living tissue not in need of such heat treatment into the deposit of material when the deposit of material is positioned in the living tissue adjacent the tissue in need of heat treatment, said radio frequency radiation having a wavelength when passing through the living tissue not in need of such heat treatment; wherein
   the diameter of the deposit of material is within a range of about 0.5 times to about 0.16 times the wavelength of the radio frequency signal within the living tissue not in need of heat treatment and at least one of the dielectric constant and the conductivity of the deposit of material is greater than the dielectric constant and the conductivity of the living tissue not in need of heat treatment to selectively heat the deposit of material to a temperature greater than the surrounding tissue not in need of heat treatment at least partially through resonant heating of the deposit of material from the radio frequency signal, the heated deposit of material then supplying heat for heat treatment to the tissue adjacent the deposit of material.

12. Apparatus for providing heat treatment to living tissue in need of such treatment and surrounded by living tissue not in need of such treatment according to claim 11, wherein the deposit of material includes a container with a filler material held within the container.

13. Apparatus for providing heat treatment to living tissue in need of such treatment and surrounded by living tissue not in need of such treatment according to claim 12, wherein the container is an elastic material.

14. Apparatus for providing heat treatment to living tissue in need of such treatment and surrounded by living tissue not in need of such treatment according to claim 13, wherein the container is an inflatable balloon.

15. Apparatus for providing heat treatment to living tissue in need of such treatment and surrounded by living tissue not in need of such treatment according to claim 14, wherein the inflatable balloon includes an inflation inlet.

16. Apparatus for providing heat treatment to living tissue in need of such treatment and surrounded by living tissue not in need of such treatment according to claim 15, wherein the inflatable balloon is mounted to the distal end portion of a catheter and the inflation inlet to the balloon is from a catheter inflation passage.

17. Apparatus for providing heat treatment to living tissue in need of such treatment and surrounded by living tissue not in need of such treatment according to claim 16, wherein the filler material held within the container is an inflation fluid held within the inflatable balloon, and wherein the inflatable balloon is inflatable by passing the inflation fluid into the balloon through the catheter inflation passage.

18. Apparatus for providing heat treatment to living tissue in need of such treatment and surrounded by living tissue not in need of such treatment according to claim 17, wherein the inflation fluid is saline solution.

19. Apparatus for providing heat treatment to living tissue in need of such treatment and surrounded by living tissue not in need of such treatment according to claim 18, wherein the deposit of material is adapted to be implanted into the living tissue.

20. Apparatus for providing heat treatment to living tissue in need of such treatment and surrounded by living tissue not in need of such treatment according to claim 19, wherein the deposit is implanted into the living tissue by inserting the distal end portion of the catheter into the living tissue.

21. Apparatus for providing heat treatment to living tissue in need of such treatment and surrounded by living tissue not in need of such treatment according to claim 20, wherein the catheter additionally includes an insertion passage extending along the catheter to a position aligned with the inside of the balloon.

22. Apparatus for providing heat treatment to living tissue in need of such treatment and surrounded by living tissue not in need of such treatment according to claim 21, wherein the insertion passage is adapted to receive a temperature sensing probe with a temperature sensor positioned inside the insertion passage aligned with the inside of the balloon.

23. Apparatus for providing heat treatment to living tissue in need of such treatment and surrounded by living tissue not in need of such treatment according to claim 21, wherein the insertion passage is adapted to alternately receive a high dose radiation emitter and a temperature sensing probe.

24. Apparatus for providing heat treatment to living tissue in need of such treatment and surrounded by living tissue not in need of such treatment according to claim 21, wherein the insertion passage is adapted to receive the source of radio frequency radiation positioned inside the insertion passage at a position aligned with the inside of the balloon.

25. Apparatus for providing heat treatment to living tissue in need of such treatment and surrounded by living tissue not in need of such treatment according to claim 11, wherein the source of radio frequency radiation is positioned within the deposit to direct radio frequency radiation through the deposit toward the surrounding tissue not in need of treatment.

26. Apparatus for providing heat treatment to living tissue in need of such treatment and surrounded by living tissue not in need of such treatment according to claim 1, wherein the source of radio frequency radiation is an applicator including a cavity for receiving a body part therein and having a radio frequency antenna operable to direct radio frequency radiation into the body part received in the cavity.

27. Apparatus for providing heat treatment to living tissue in need of such treatment and surrounded by living tissue not in need of such treatment according to claim 11, wherein the radio frequency antenna is an antenna array operable to direct a circularly polarized radio frequency electromagnetic field into the deposit.

28. A method for providing heat treatment to living tissue in need of such treatment and surrounded by living tissue not in need of such heat treatment with the tissue not in need of such treatment having a dielectric constant and a conductivity, comprising:
   inserting a deposit of material in the living tissue adjacent the tissue in need of heat treatment, said deposit having a size, dielectric constant, and conductivity with at least one of the dielectric constant and conductivity being greater than the dielectric constant and conductivity of the tissue not in need of heat treatment; and directing radio frequency radiation into the deposit, said radio frequency radiation having a wavelength within the living tissue not in need of such heat treatment;

wherein a diameter of the deposit is within a range of about 0.5 times to 0.16 times the wavelength of the radio frequency signal within the living tissue not in need of such heat treatment.

29. A method of treating breast cancer comprising:

performing a lumpectomy to remove a cancerous tumor from the breast resulting in a cavity in the breast from where the cancerous tumor was removed which is surrounded by fatty mammary tissue, said fatty mammary tissue having a dielectric constant and a conductivity;

inserting a deposit of material within the cavity adjacent tissue surrounding the cavity, said deposit material having a dielectric constant and conductivity with at least one of the dielectric constant and conductivity greater than the dielectric constant and conductivity of the fatty mammary tissue;

directing radio frequency radiation into the deposit, said radio frequency radiation having a wavelength within the surrounding fatty mammary tissue; wherein a diameter of the deposit is within a range of about 0.5 times to 0.16 times the wavelength of the radio frequency signal within the fatty mammary tissue, the heated deposit then providing hyperthermia treatment to the tissue adjacent the cavity.

30. A method of treating breast cancer according to claim 29, additionally including the step of applying radiation to the tissue in need of treatment, and coordinating the step of applying the radiation and the step of providing hyperthermia treatment so that the hyperthermia treatment increases the effectiveness of the radiation treatment.

31. A method of treating breast cancer according to claim 29, additionally including the step of applying chemotherapy to the tissue in need of treatment, and coordinating the step of applying the chemotherapy and the step of providing hyperthermia treatment so that the hyperthermia treatment increases the effectiveness of the chemotherapy.

* * * * *